(12) United States Patent
Walton

(10) Patent No.: US 9,201,047 B1
(45) Date of Patent: Dec. 1, 2015

(54) CONTINUOUSLY ADAPTIVE ULTRASONIC INSPECTION DEVICE

(71) Applicant: The Boeing Company, Chicago, IL (US)

(72) Inventor: Steven Ray Walton, Buckley, WA (US)

(73) Assignee: The Boeing Company, Chicago, IL (US)

(*) Notice: Subject to any disclaimer, the term of this patent is extended or adjusted under 35 U.S.C. 154(b) by 384 days.

(21) Appl. No.: 13/910,160

(22) Filed: Jun. 5, 2013

(51) Int. Cl.
  *G01N 29/34* (2006.01)
  *G01N 29/24* (2006.01)

(52) U.S. Cl.
  CPC ...................................... *G01N 29/24* (2013.01)

(58) Field of Classification Search
  None
  See application file for complete search history.

(56) References Cited

U.S. PATENT DOCUMENTS

| | | | |
|---|---|---|---|
| 4,774,842 A * | 10/1988 | Kollar et al. | 73/640 |
| 4,807,476 A | 2/1989 | Cook et al. | |
| 6,658,939 B2 | 12/2003 | Georgeson et al. | |
| 7,430,913 B2 | 10/2008 | Sarr | |
| 7,516,664 B2 | 4/2009 | Meier et al. | |
| 7,617,732 B2 | 11/2009 | Bui et al. | |
| 7,698,947 B2 | 4/2010 | Sarr | |
| 7,836,768 B2 | 11/2010 | Young et al. | |

* cited by examiner

*Primary Examiner* — Robert R Raevis
(74) *Attorney, Agent, or Firm* — Ostrager Chong Flaherty & Broitman P.C.

(57) ABSTRACT

A system and method for inspecting a joint fillet having a surface whose radius varies along the length of the joint fillet. In one embodiment, the inspection apparatus comprises: a chassis; a shoe assembly supported by the chassis and comprising an axle; a transducer array assembly translatably coupled to the shoe assembly; biasing means for urging the transducer array assembly to translate relative to the shoe assembly in a first direction; and a lever assembly pivotably coupled to the axle of the shoe assembly and in contact with the transducer array assembly over a range of angular positions of the lever assembly. The transducer array will translate in a second direction opposite to the first direction when the net force exerted by the lever assembly is greater than the biasing force exerted by the biasing means. The lever assembly is used to automatically adjust the array position to the varying fillet radius.

21 Claims, 17 Drawing Sheets

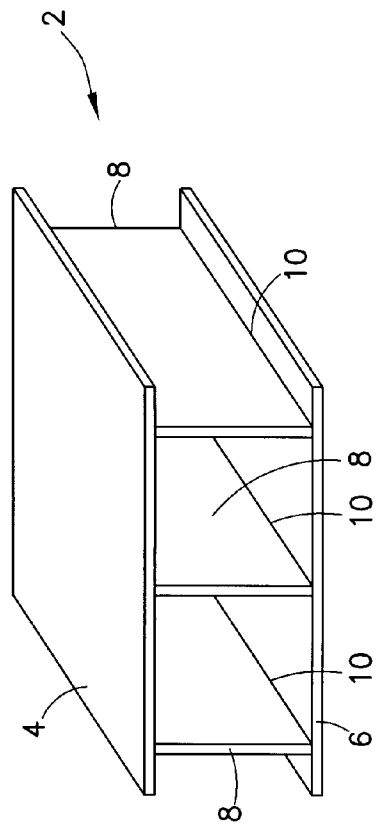
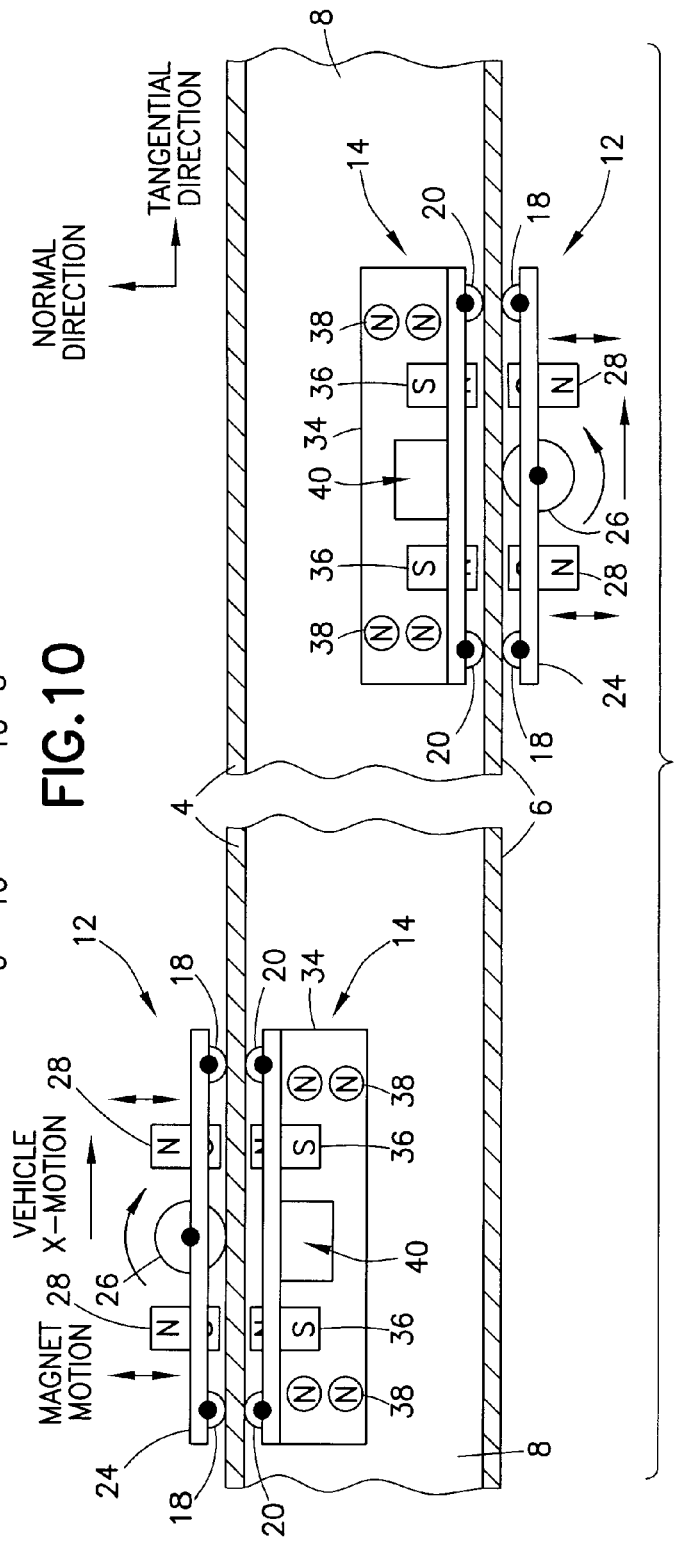
FIG.10
FIG.11

CONTINUOUSLY ADAPTIVE ULTRASONIC INSPECTION DEVICE

BACKGROUND

This disclosure generally relates to equipment and methods for non-destructive inspection, and more particularly relates to methods and apparatus for inspecting structures having irregular and variable shapes, especially soft-tooled structures made of composite material.

A variety of elongated composite structures may have relatively confined internal cavities that require inspection in order to assure that the structure meets production and/or performance specifications. Conventional composite structure cured with hard tooling results in composite radii that are well defined and repeatable. In contrast, the composite radii formed using soft tooling are not always well defined and may vary from part to part. In some cases, dimensional or contour variations may be greater than those that would result from using hard tooling. These larger variations make reliable inspection using conventional methods more challenging. In view of the deviation from circularity of soft-tooled composite radii, the term "radiused surface" as used hereinafter should be construed non-strictly to include surfaces that vary from being a section of a circular cylinder.

Critical composite structure in aerospace and potentially in applications outside aerospace must be inspected to required specifications to ensure structural integrity. Inspecting soft-tooled composite structures presents distinct yet interrelated challenges. Critical inspection areas include the radiused surfaces of composite part joint fillets. Moreover, such soft-tooled surfaces must be inspected in a production environment. For a production inspection, the inspection rate must be sufficient to meet the part production rate.

For ultrasonic inspection of composite structure, the ultrasound beam should ideally enter at 90 degrees to the local surface of the composite part being inspected. If it does not enter at 90 degrees, it will be refracted off normal and a return echo from any possible internal structure or anomaly will not be optimum. Traditionally a 90-degree entry angle is maintained by holding a sensor array at a precisely fixed position in space relative to the surface. While this works well for known surfaces, such as flat or cylindrical surfaces of a given, fixed radius and circular shape, this approach will not provide adequate results for surfaces which are, for example, parabolic, irregular, or of varying radius of not necessarily cylindrical cross section. Traditional methods of interrogating such a radius with ultrasound fail to keep the sound path sufficiently perpendicular over the entire inspection area.

Current practice in inspecting composite part joint fillets consists of sliding a probe that is geometrically aligned to a fixed fillet radius along the joint. If the radius changes away from this fixed alignment, the data becomes unusable. To realign to the new geometry, a physically different probe can be substituted or an adaptable probe can be manually readjusted. The readjustment or complete replacement, of the ultrasonic probe(s) during the operation slows the inspection process time dramatically.

There is a need for an automated solution to the problem of inspecting composite parts with radii that vary along the length of the part in which the sensor energy enters the composite part volume very close to the local perpendicular at the inspection site.

SUMMARY

The system and method disclosed herein enables the ultrasonic inspection of variable and irregular shapes. An example of a primary use of this scanning system would be for the inspection of a variable radius or a noncircular radius produced using soft tooling to form a composite structure, such as an integrally stiffened wing box of an aircraft. During non-destructive inspection of composite part joint fillets, the device disclosed herein automatically adapts (i.e., is self-adjusting) to radii that change dimension along the length of the joint. The disclosed device produces reliable ultrasonic inspection data by mechanically adjusting itself to the as-manufactured fillet of an intersection as the device is moved along the joint. This self-adjustment capability speeds up the inspection process to a significant degree (an order of magnitude or more), and enables the use of automation. In many applications, multiple probes can be replaced by a single adaptive probe, saving inspection time, cost of installation, and cost of maintenance. An angle-adaptive version has the potential to replace a large number of existing probes with one device.

One aspect of the subject matter disclosed in detail below is an inspection apparatus comprising: a chassis; a shoe assembly which is supported by the chassis, the shoe assembly comprising an axle; a transducer array assembly which is translatably coupled to the shoe assembly; first biasing means for urging the transducer array assembly to translate relative to the shoe assembly in a first direction; and a lever assembly which is pivotably coupled to the axle of the shoe assembly and which contacts the transducer array assembly over a range of angular positions of the lever assembly. The transducer array will translate in a second direction opposite to the first direction when the net force exerted by the lever assembly is greater than the biasing force exerted by the first biasing means. (As used herein, the term "translatably coupled" refers to a coupling of parts in which one part can move linearly relative to the other part, whether by sliding, rolling or other means.)

In accordance with some embodiments, the lever assembly comprises a lever, the lever comprising a distal portion in contact with the transducer array assembly, a proximal portion pivotably coupled to the axle, and an intermediate portion which connects the distal and proximal portions. In accordance with other embodiments, the lever assembly comprises: a lever comprising a distal portion, a proximal portion pivotably coupled to the axle, and an intermediate portion which connects the distal and proximal portions; and a first wheel rotatably coupled to the distal portion of the lever and in contact with the transducer array assembly. The following optional features can be implemented regardless of whether the lever contacts the transducer array assembly or carries a first wheel that contacts the transducer array assembly. (A) The intermediate portion of the lever may have a curved surface that projects outside the shoe assembly. (B) The apparatus may further comprise a second wheel which is rotatably coupled to the intermediate portion of the lever, wherein a portion of the second wheel projects outside the shoe assembly. (C) The apparatus may further comprise a carriage translatably coupled to the lever, second biasing means for urging the carriage to translate toward the proximal portion of the lever, and a second wheel rotatably coupled to the carriage, wherein a portion of the second wheel projects outside the shoe assembly.

In the case of option (C), the chassis comprises: first and second carriages; a first fixed pivot which pivotably couples the first carriage to the second carriage; first and second links each having first and second ends; a second fixed pivot which pivotably couples the first carriage to the first end of the first link; a third fixed pivot which pivotably couples the second carriage to the first end of the second link; a floating pivot which pivotably couples the second end of the first link to the second end of the second link; a flange angle transfer link which translates in tandem with the floating pivot; a fulcrum cone which is translatably coupled to the first axle of the shoe assembly and which is in contact with the flange angle transfer link and the second wheel; and third biasing means for urging the fulcrum cone into contact with the flange angle transfer link.

Another aspect of the disclosed subject matter is an inspection system comprising: a chassis comprising a plurality of rolling elements having respective axes of rotation which are perpendicular to a rolling direction of the chassis; a shoe which is supported by the chassis; a transducer array which is translatably coupled to and carried by the shoe; biasing means for producing a biasing force that urges the transducer array to translate relative to the shoe in a first direction; and surface follower cam means arranged to exert a net force that opposes the biasing force, wherein the surface follower cam means are pivotably coupled to the shoe. The transducer array will translate in a second direction opposite to the first direction when the net force exerted by the surface follower cam means is greater than the biasing force. This arrangement enables the non-destructive inspection of joint fillets of parts made of composite material, which joint fillets have a radiused surface whose radius varies along the length of the fillet. The surface follower cam means contact the fillet surface as the apparatus travels along the length of the joint fillet and deflect as the radius of the fillet changes.

A further aspect of the subject matter disclosed herein is an inspection apparatus comprising: a chassis comprising a plurality of rolling elements having respective axes of rotation which are perpendicular to a rolling direction of the chassis; a shoe assembly which is supported by the chassis; a transducer array assembly which is translatably coupled to the shoe assembly; one or more springs that urge the transducer array assembly to translate relative to the shoe assembly in a first direction normal to the rolling direction; and one or more levers which are rotatable relative to the shoe assembly through a range of angular positions for causing the transducer array to translate in a second direction opposite to the first direction. The transducer array translates in the second direction when a first net force exerted by the one or more levers is greater than and opposite to a second net force exerted by the one or more springs. In accordance with one embodiment, the shoe assembly comprises a shoe and first and second slide rods, and the transducer array assembly comprises an array support structure, a transducer array attached to the array support structure, and first and second linear bearings respectively slidable along the first and second slide rods. When the first and second levers are deflected inward by contact with a fillet surface, the levers push the transducer array in a second direction opposite to the first direction.

Yet another aspect is a method for inspecting a joint fillet having a surface the radius of which varies along a length of the joint fillet, performed using an inspection unit comprising a shoe and a curved transducer array that is movable relative to the shoe and has a center. The method comprises: (a) activating a motor to cause the inspection unit to move along the length of the joint fillet from a first longitudinal position, whereat the curved transducer array is directed toward a first target portion of the joint fillet having a surface with a first radius, to a second longitudinal position, whereat the curved transducer array is directed toward a second target portion of the joint fillet having a surface with a second radius different than the first radius; (b) during step (a), continuously moving the curved transducer array relative to the shoe so that the center of the curved transducer array and the center of the variable radius of the joint fillet are the same point in space; and (c) activating the curved transducer array when the inspection unit is in the first and second longitudinal positions to interrogate the first and second target positions respectively. The curved transducer array moves relative to the shoe in response to a varying force produced by contact with portions of the surface of the joint fillet which vary in radius. In accordance with one embodiment, the distance that the curved transducer array is moved relative to the shoe during step (a) is equal to the product of a factor times a difference between a first distance of a center of the first radius of the joint fillet from a reference line and a second distance of a center of the second radius of the joint fillet from the reference line.

Other aspects are disclosed and claimed below.

BRIEF DESCRIPTION OF THE DRAWINGS

FIG. 10 is a diagram showing an orthographic view of a portion of a generalized integrally stiffened wing box of an airplane having top and bottom skins or panels connected by a plurality of spars.

FIG. 11 is a diagram showing a side view of a tractor-trailer configuration that includes an active trailer vehicle above and a tractor vehicle below a bottom skin of an integrally stiffened wing box. (A passive trailer vehicle on the other side of the spar is not visible.) The left-hand side of FIG. 11 shows an inspection scenario wherein the trailer vehicles are inverted, while the right-hand side shows an inspection scenario wherein the tractor vehicle is inverted.

DETAILED DESCRIPTION

Figure 1A:
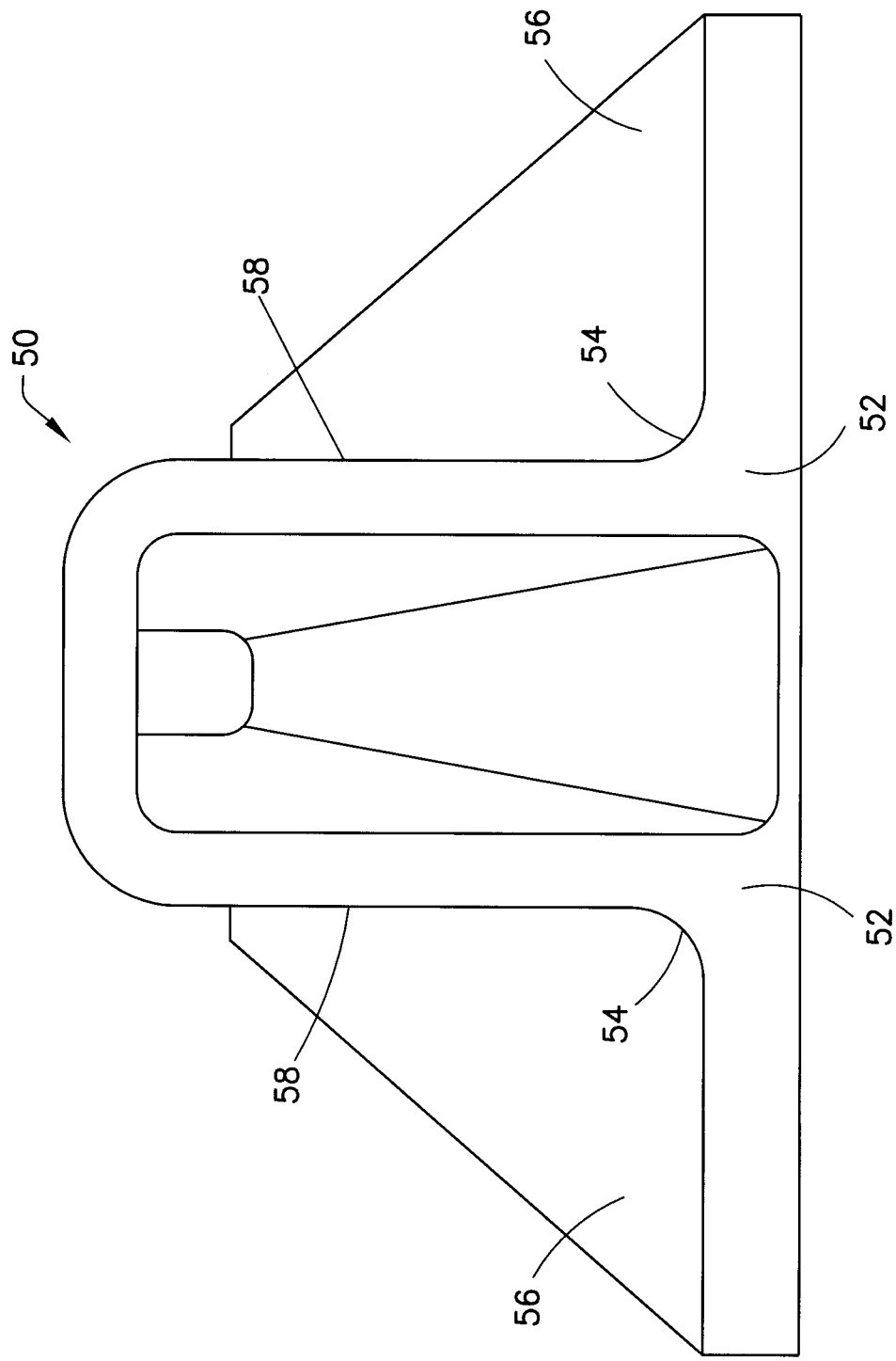
FIG. 1A is a diagram showing a cross-sectional view of a composite part having joint fillets whose radii vary along the length of the joint fillet.
Figure 1B:
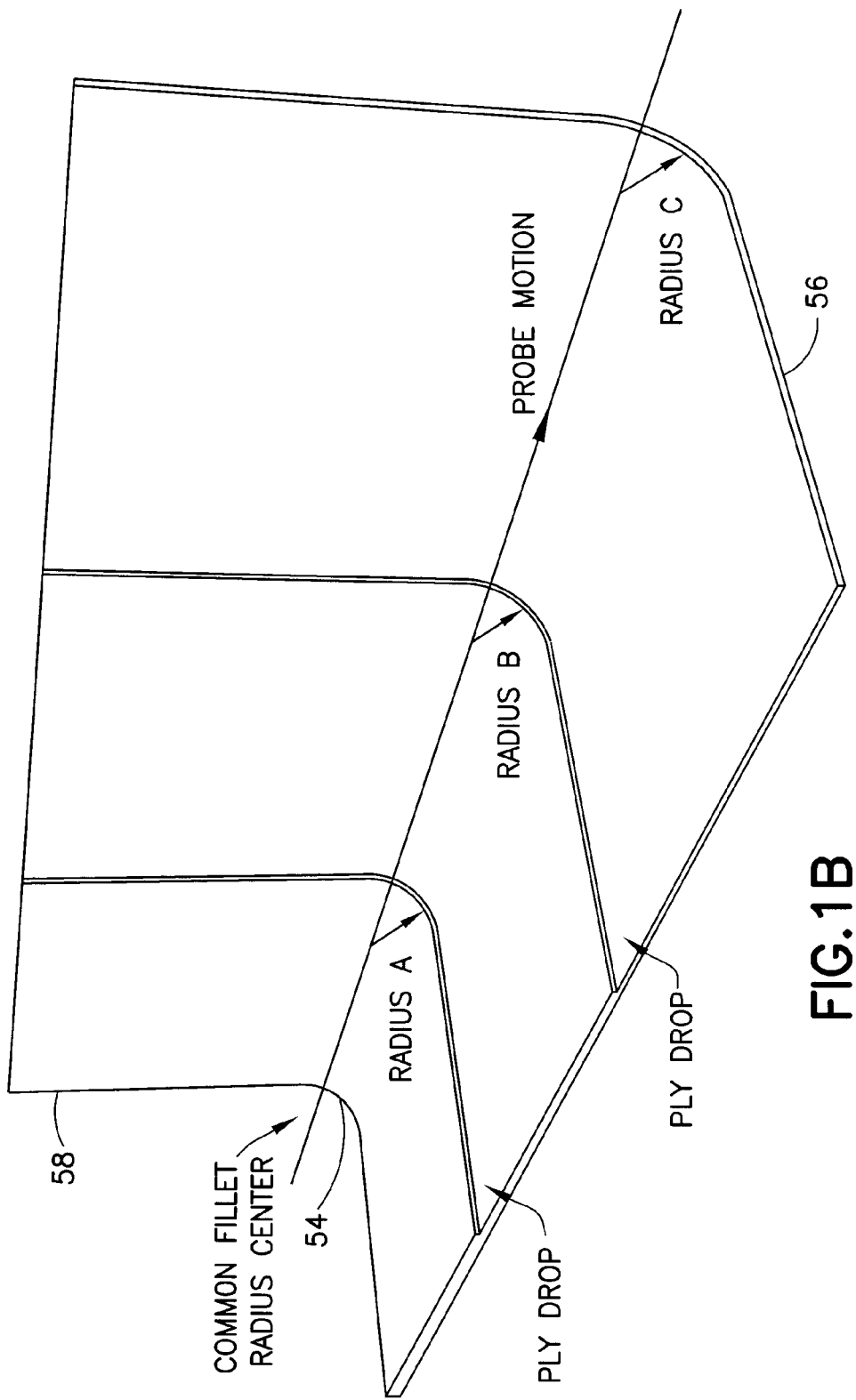
FIG. 1B is a diagram showing an isometric view of a portion of a composite part having a joint fillet with a radius of variable and unknown shape due to dropping of plies. The arrow indicates a direction of travel of the radius scanner disclosed herein during inspection of the radius, which direction will be referred to herein as the X-direction.

An apparatus and a method for non-destructive inspection of composite part joint fillets will now be described. FIG. 1A shows a cross section of a component 50 comprising a pair of vertical spars 58 which respectively intersect a pair of flanges 56 at respective joints 52. Each joint has a fillet 54 of radius. The fillet radius along any particular joint may be fixed at some value, or may vary along its length as plies are added or subtracted. FIG. 1B shows plies being dropped resulting in an increasing fillet radius in the direction of the probe motion. When inspecting such joints with a curved ultrasonic transducer array, it is important that the designed "center" of the array be positioned at the geometric center of the fillet radius (i.e., the common center of the fillet plies).

The probe disclosed below may, for example, be applied in the inspection of soft-tooled composite parts, such as wing boxes comprising top and bottom external skins connected by a multiplicity of spars. The filleted join regions (i.e., radii) of such parts, whether they are designed to be constant or to vary by part location, will "vary by manufacturing". This fact creates a difficult and unique mechanical challenge to design and build an apparatus that can maintain sensor-to-part surface normality over a challenging and not-known-in-advance variety of "radial" shapes. In accordance with one implementation, the ability to maintain normality over an unknown "radius" is provided using the mechanical design described hereinafter.

Figure 2:
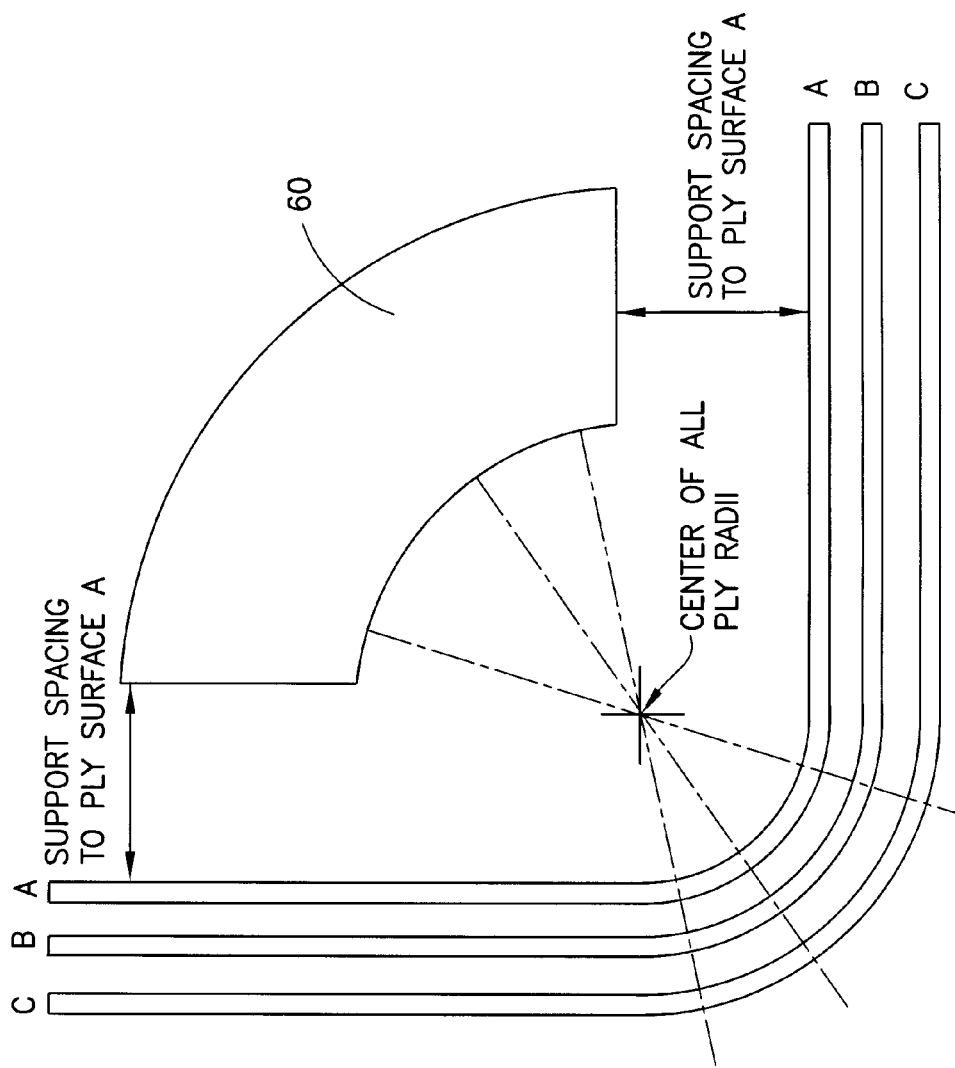
FIG. 2 is a diagram showing a normal probe alignment in which a center of a curved transducer array and a common center (indicated by a "+" symbol) of three fillet radii (i.e., the radii of plies A, B and C) are the same point in space.

In accordance with the teachings herein, a probe design is provided which is sensitive to the radius of the fillet at any current probe location along a part joint, and positions a curved ultrasonic array 60 (see FIG. 2) at the proper position such that the common center of the fillet radii (e.g., the radii of plies A, B and C) and the center of the array 60 are the same point in space, indicated by the "+" symbol in FIG. 2. This feature ensures that the direction of ultrasound entry will be normal to the confronting radiused surface.

In the situation depicted in FIG. 2, respective supports (not shown) are provided which contact the surface of ply A and maintain the curved ultrasonic transducer array 60 at a position whereat the array center and the common center of the fillet radii are the same point in space. In this case, each return beam (not shown) will be reflected back to the respective transducer that transmitted the respective interrogating beam.

Figure 3:
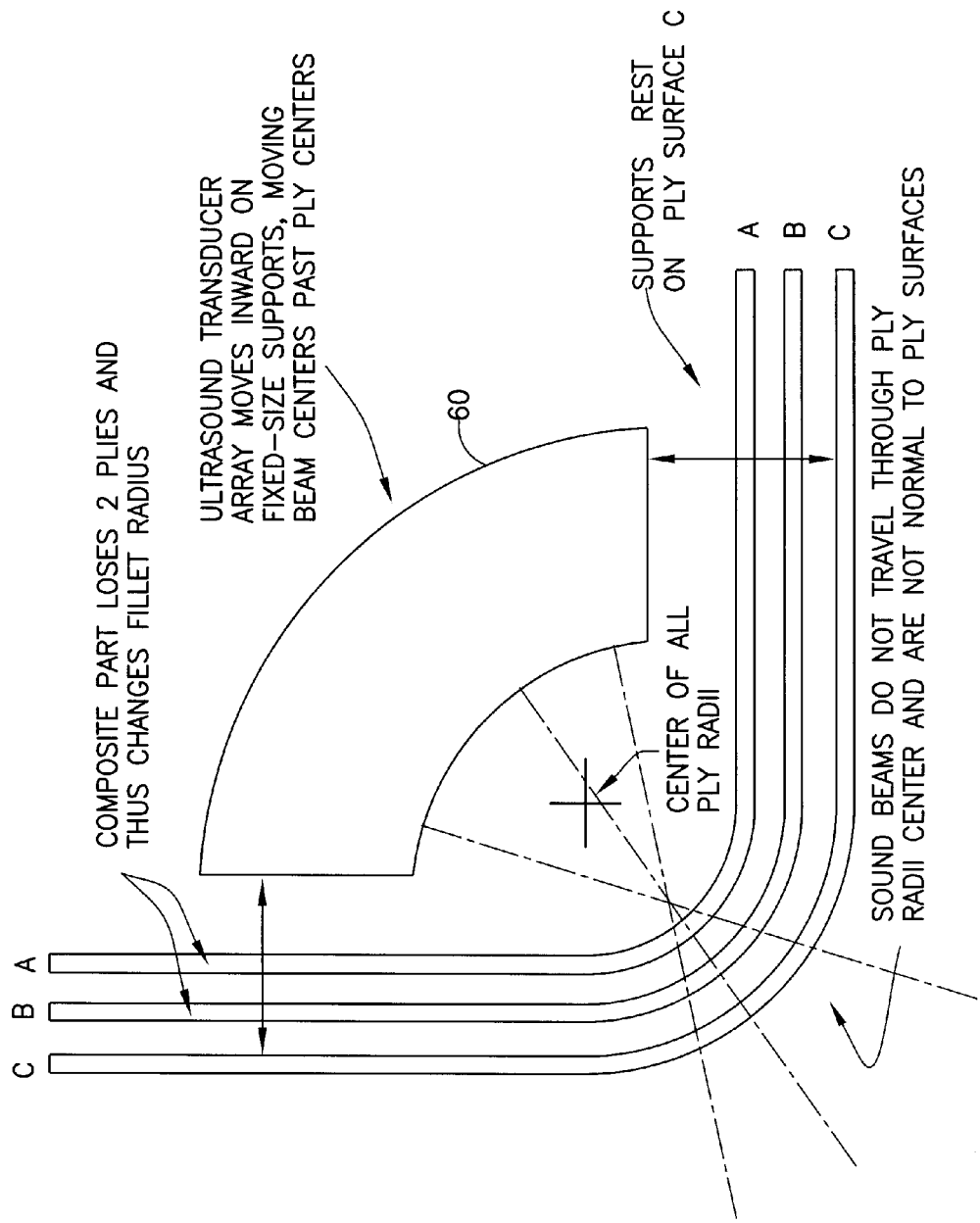
FIG. 3 is a diagram showing a probe alignment in which a center of a curved transducer array and a common center (indicated by a "$\underset{+}{\cdot}$" symbol) of three fillet radii (i.e., the radii of plies A, B and C) are not the same point in space.

In contrast, FIG. 3 shows a situation wherein the curved ultrasonic transducer array has traveled to a position along the composite part whereat plies A and B have been dropped (ply dropping is shown in FIG. 1B), whereat the supports now contact ply C. If the supports have fixed lengths, then the result of those supports being in contact with ply C (as seen in FIG. 3) instead of ply A (as seen in FIG. 2) is that the ultrasonic transducer array 60 has now changed its position vis-à-vis (i.e., moved closer to) the joint fillet, which causes the array center to move away (i.e., radially inward) from the common center of the ply radii. The result is a mismatch because the ultrasonic transducer array 60 has been designed to a radius that does not match the fillet of the part being inspected.

The probe design disclosed herein positions a curved ultrasonic array at a proper position such that the common center of the fillet radii and the center of the array are the same point in space. To explain how this is accomplished, certain geometric characteristics of a fillet will be described with reference to FIGS. 4 and 5.

The simplest support method for an ultrasonic probe shoe 62 (a frame that physically contacts with the part surface while supporting the curved ultrasonic transducer array) is to use a fixed frame with rollers or skids 64 and 66 that follow along the two flange surfaces that form a joint. Rollers may be simple bearings. Alternatively, air bearings or hydraulic (water-driven) bearings can be utilized. In any case, the result is that the shoe 62 is always spaced away from the respective flange surface by a respective fixed distance and orientation, as depicted in FIG. 4.

To facilitate adjusting the transducer position as a function of the fillet radius, it is helpful to visualize varying radii between two fixed surfaces (invariant in relation to the shoe geometry), instead of stacked surfaces and radii (as shown in FIGS. 2 and 3, usually drawn this latter way because that is how stacked plies appear in cross sections of actual parts). FIG. 4 is arranged with invariant surfaces, showing how the fillet surface and radius center vary, from the point of view of a fixed ultrasonic probe shoe 62.

Figure 4:
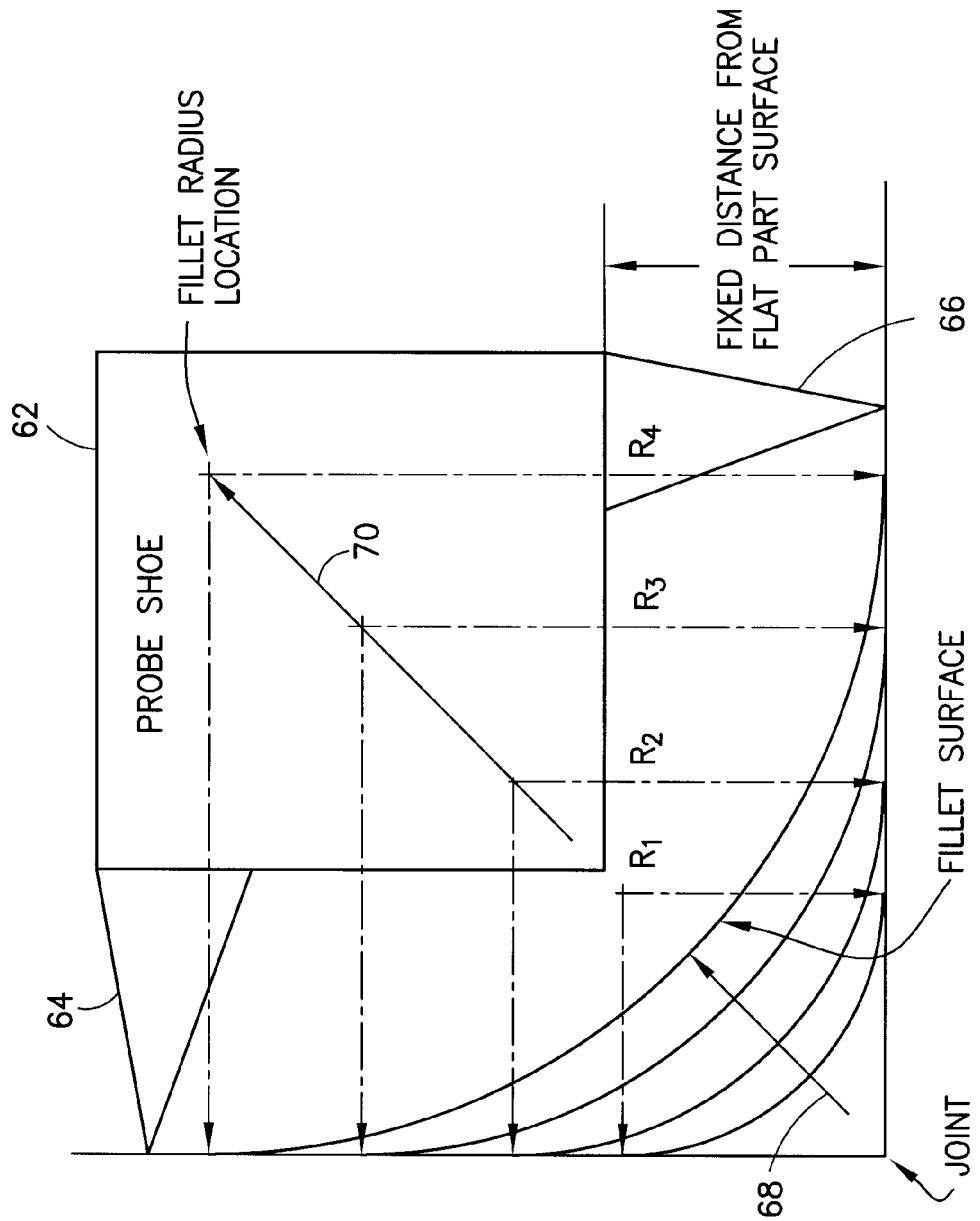
FIG. 4 is a diagram showing a fillet shape with invariant surface positions.

As seen in FIG. 4, as the surface of the fillet approaches the shoe with increasing radius (as indicated by arrow 68), the center of the radius moves along a diagonal through the shoe (as indicated by arrow 70). It is this motion which the transducer array focus (i.e., center) must track. One way to implement such tracking is to determine the functional relationship between the motion of the fillet surface, along the diagonal (arrow 68), and the motion of the fillet center (i.e., the common center of the fillet ply radii) (arrow 70). If the functional relationship is a constant (i.e., one is directly proportional to the other), then the array can be pushed along a diagonal linear axis with a simple lever (not shown in FIG. 4).

Figures 5, 5A:
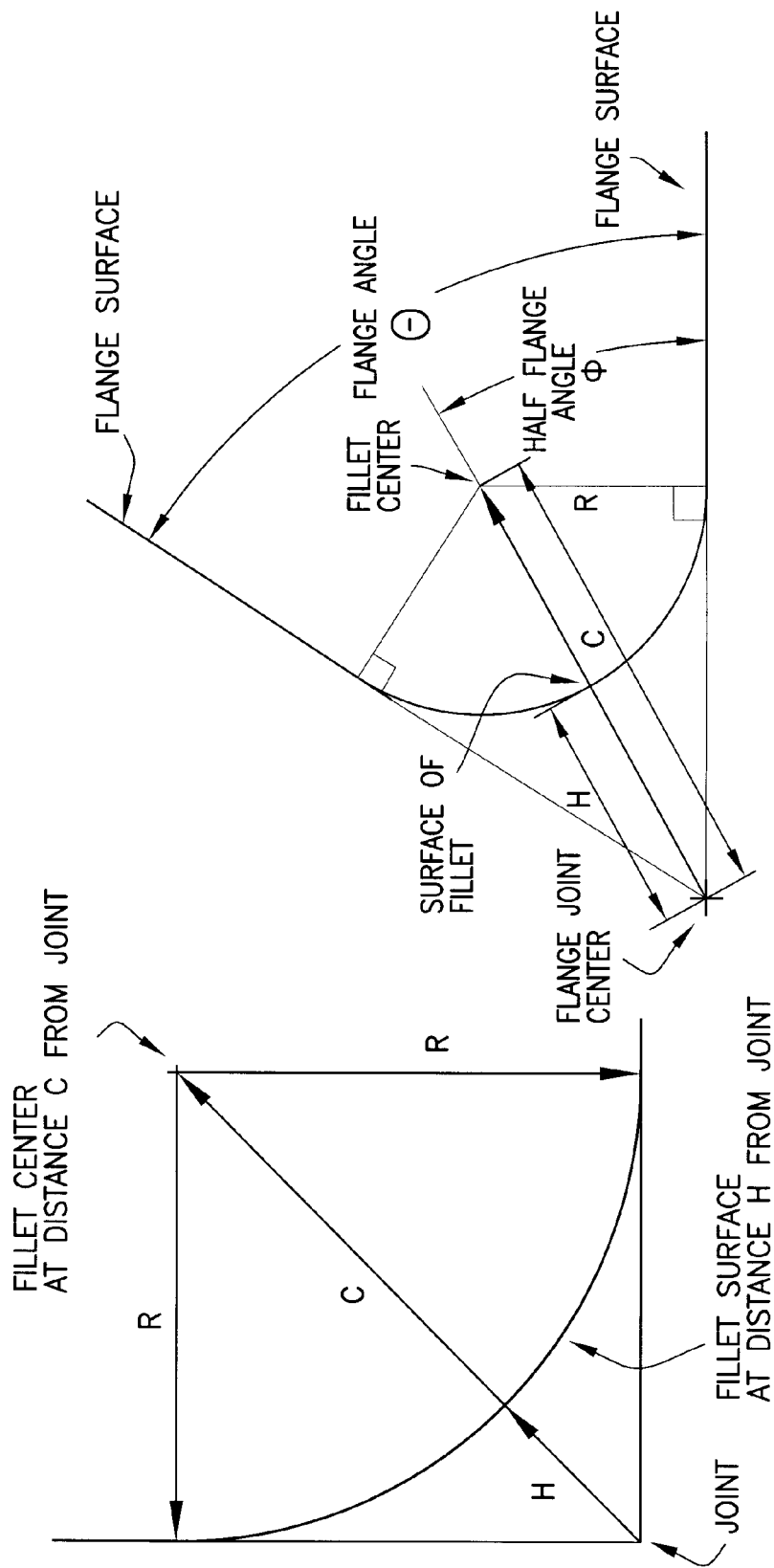
FIG. 5 is a diagram showing various parameters which are used to calculate the relative motion of a location of a fillet surface and a location of the center of the fillet surface when the flange angle is 90°. (These parameters also appear in Eqs. (1) through (5) discussed below.)
FIG. 5A is a diagram showing various parameters which are used to calculate the relative motion of a location of a fillet surface and a location of the center of the fillet surface when the flange angle is other than 90°. (These parameters also appear in Eqs. (6) through (8) discussed below.)

FIG. 5 illustrates this analysis for the restricted case where the flange angle between the two flange surfaces is 90° (the general case will be discussed below). First, the following two equations governing the location of the fillet surface H and the fillet center C (in the direction of the diagonal bisecting the two surfaces) are derived from simple geometry:

$$C = \sqrt{2}R \quad (1)$$

$$H = (\sqrt{2} - 1)R \quad (2)$$

These parameters are differentiated once to provide the rates of motion as a function of changing fillet radius R:

$$dC/dR = \sqrt{2} \qquad (3)$$

$$dH/dR = \sqrt{2} - 1 \qquad (4)$$

Then the rate of motion of C along R is simply divided by the rate of motion of H along R to get the relative rate of motion between C and H, as follows:

$$dC/dH = dCdR/dRdH = \sqrt{2}/\sqrt{2} - 1 \approx 3.414 \qquad (5)$$

The result is a simple constant of approximately 3.414. This is the rate at which, along the direction of the angle bisector, the center of the fillet radius moves away from the joint intersection compared to the rate at which the surface of the fillet moves along the same vector.

Figure 6:
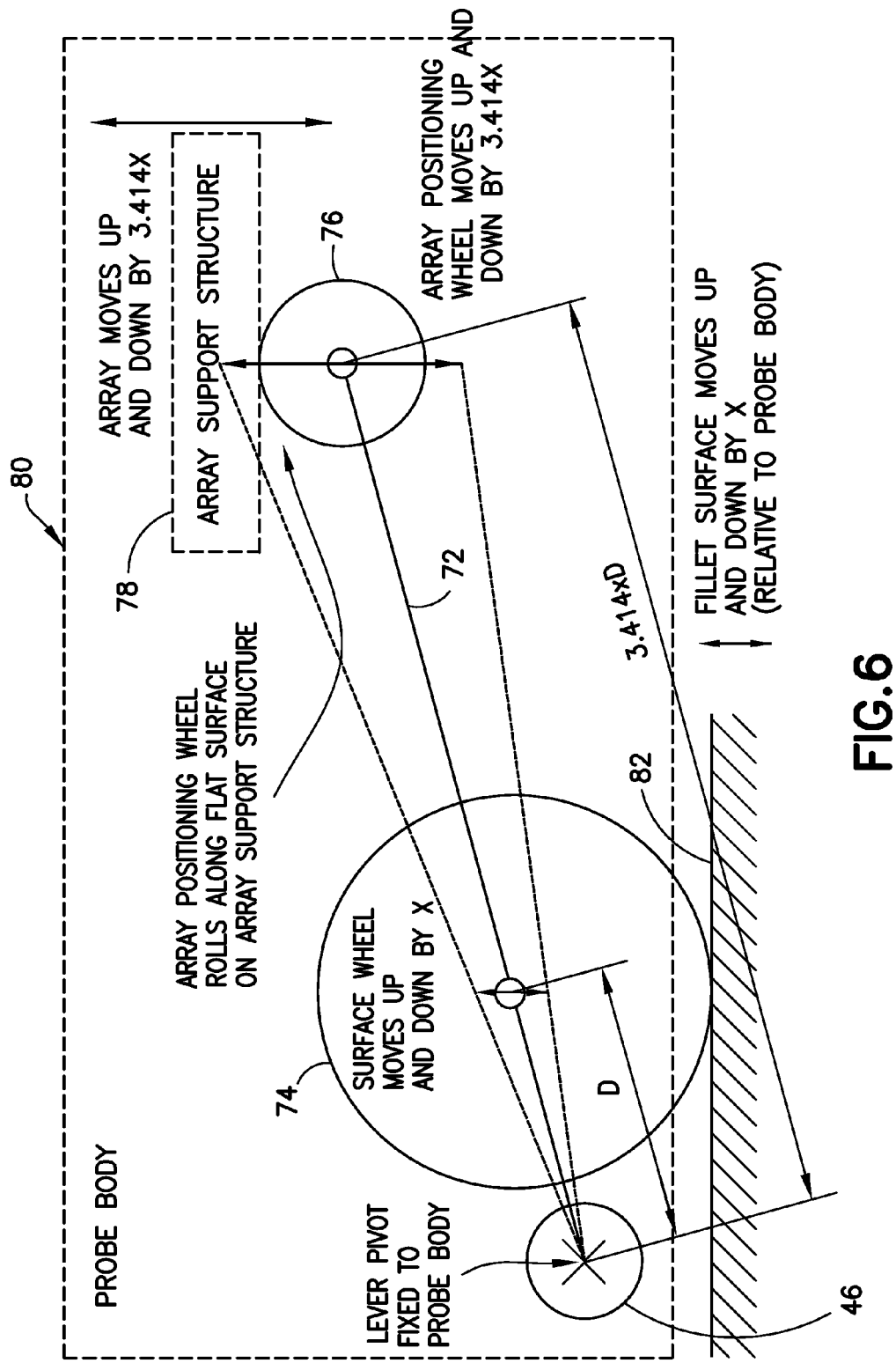
FIG. 6 is a diagram showing a principle of operation of a lever design for causing correct relative motion of a fillet surface and an ultrasonic transducer array for cases when the flange angle is 90°.

The foregoing direct proportionality (involving multiplication by a factor) can be mechanized by a simple lever or cam (schematically represented by line 72 in FIG. 6) having a proximal portion that is pivotably mounted to an axle 46 which is supported by a probe shoe or body 80. In accordance with the embodiment schematically depicted in FIG. 6, a surface wheel 74 is rotatably coupled to an intermediate portion of the lever 72 and an array positioning wheel 76 is rotatably coupled to a distal portion of the lever 72. The surface wheel 74 bears against and rolls along the fillet surface 82, while the array positioning wheel 76 bears against and rolls along a flange surface of a transducer array support structure 78. The transducer array support structure 78 is translatably coupled to the probe shoe or body 80. As the fillet surface 82 moves up or down by a distance X, the array positioning wheel 76 (and the array support structure 78 in contact therewith) moves up or down by a distance 3.414X Thus the curved transducer array is moved toward or away from the joint intersection at a rate 3.414 times as fast as the fillet surface "moves" (i.e., changes radius), along the angle halfway between one surface and the other. This keeps the geometric alignment of the curved array with the part fillet correct. The factor 3.414 only applies in cases where the flange angle is 90°.

Figure 7A:
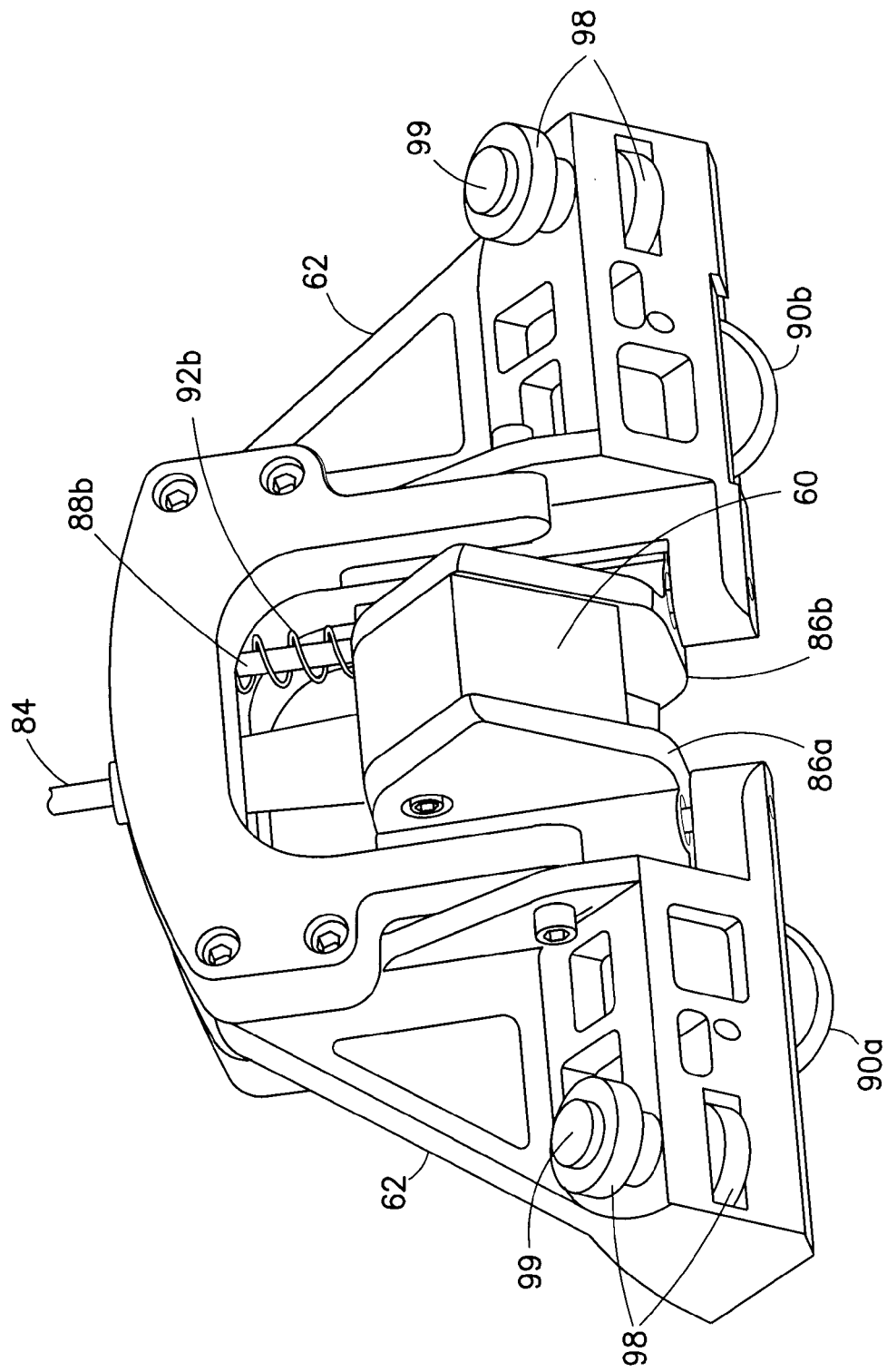
FIGS. 7A and 8A are diagrams showing isometric views of a continuously adaptive ultrasonic inspection device (in respective states) in accordance with one embodiment. The device comprises an ultrasonic transducer array translatably coupled to a probe shoe, the array being shown in its smallest fillet radius position in FIG. 7A and in its largest fillet radius position in FIG. 8A.
Figure 8A:
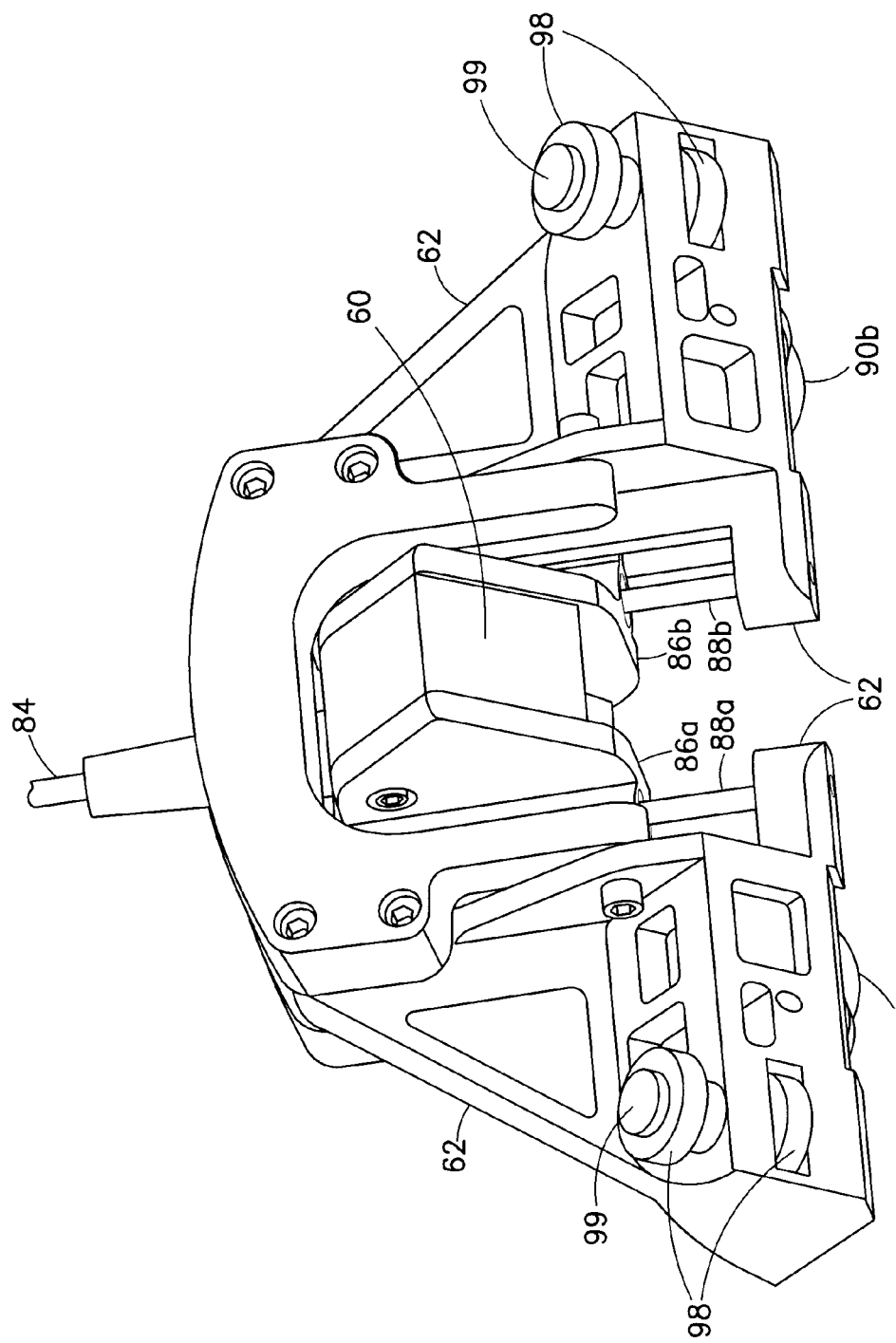

FIGS. 7A and 8A are isometric views of a continuously adaptive ultrasonic inspection device (in respective states) in accordance with one embodiment. The device comprises a curved ultrasonic transducer array 60 translatably coupled to and supported by a probe shoe 62, the array being shown in its smallest fillet radius position in FIG. 7A and in its largest fillet radius position in FIG. 8A.

In accordance with the embodiment shown in FIGS. 7A and 8A, probe shoe 62 is a rigid frame having four axles 99 (only two are visible), each axle having a pair of rollers or wheels 98 mounted thereon. The set of four wheels 98 seen in FIGS. 7A and 8A are positioned to roll against one flange surface of the composite part being inspected. Another set of four wheels (not visible in FIGS. 7A and 8A) are positioned to roll against the other flange surface of the composite part.

Figure 7B:
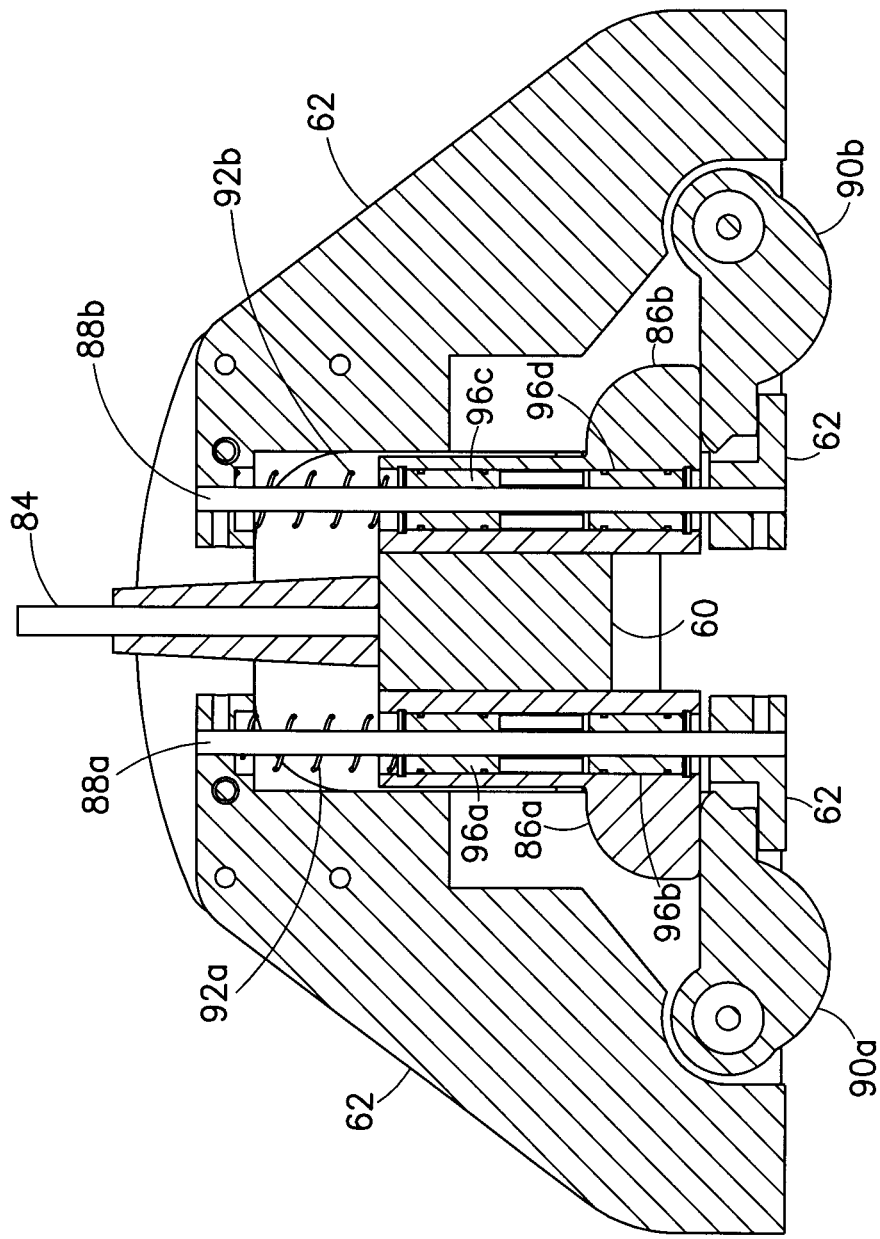
FIGS. 7B and 8B are diagrams showing cross-sectional views of the continuously adaptive ultrasonic inspection device shown in FIGS. 7A and 8A. The ultrasonic transducer array is shown in its smallest fillet radius position in FIG. 8A and in its largest fillet radius position in FIG. 8B.
Figure 8B:
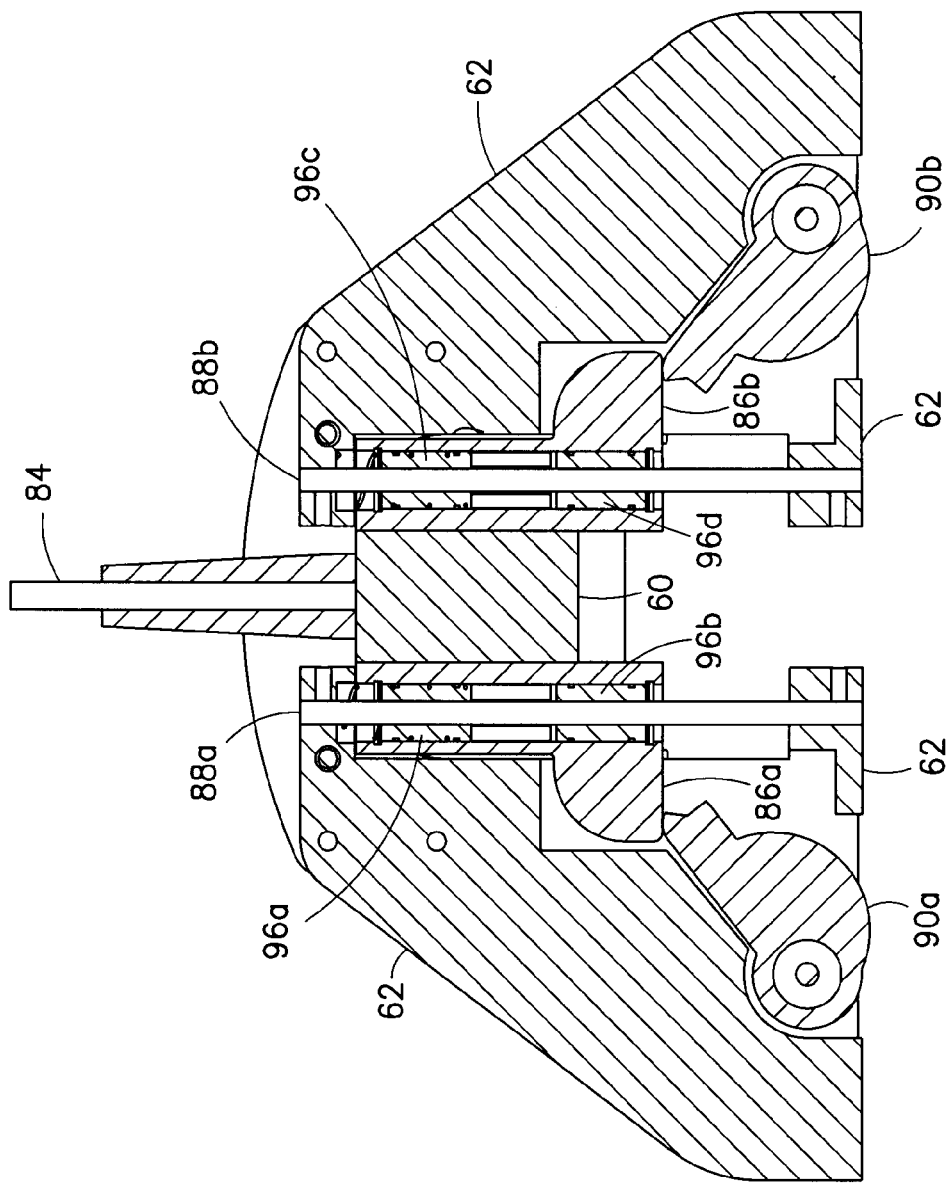

As best seen in the cross-sectional views of FIGS. 7B and 8B, the inspection device further comprises a pair of levers 90a and 90b pivotably coupled to respective axles or pins fixedly attached to the shoe 62. The levers 90a, 90b have respective curved camming surfaces which project outside the shoe 62. The curved camming surfaces of levers 90a, 90b contact the fillet surface of the composite part when the rollers 98 are in contact with respect flange surfaces having a flange angle of 90°. As the probe is moved along the fillet surface, the camming surfaces of levers 90a, 90b follow the contour of the fillet surface, causing the levers to pivot inward or outward as the number of plies at the fillet surface changes or as the radius of the fillet surface changes. This pivoting action of the levers causing the distal ends of the levers to move from the respective positions shown in FIG. 7B to the respective positions shown in FIG. 8B.

The distal ends of levers 90a, 90b are in contact with respective slide stages 86a, 86b of an array support structure to which the ultrasonic transducer array 60 is attached. The ultrasonic transducer array 60 operates under the control of an ultrasonic pulser/receiver unit (not shown) which is located at an operations command center. The ultrasonic transducer array 60 receives pulses and sends back return signals via an electrical cable 84. As the distal ends of levers 90a, 90b move from the respective positions shown in FIG. 7B to the respective positions shown in FIG. 8B, the ultrasonic transducer array 60 moves upward, i.e., further away from the joint fillet being interrogated. Based on the principle shown in FIG. 6, preferably the ultrasonic transducer array 60 is moved toward or away from the joint intersection of the composite part being inspected at a rate 3.414 times as fast as the fillet surface "moves" (i.e., changes radius), along the angle halfway between one flange surface and the other.

In accordance with the implementation depicted in FIGS. 7B and 8B, a shoe assembly comprises probe shoe 62 and a pair of mutually parallel slide rods 88a and 88b. The opposing ends of slide rods 88a, 88b are attached to respective portions of the probe shoe 62. A transducer array assembly comprises slide stages 86a, 86b of the array support structure, curved ultrasonic transducer array 60 attached to slide stages 86a, 86b, and respective sets of linear bearings 96a-96d which translatably couple the slide stages to the slide rods. More specifically, linear bearings 96a and 96b are attached to slide stage 86a and translate on slide rod 88a, while linear bearings 96c and 96d are attached to slide stage 86b and translate on slide rod 88b. A pair of compression springs 92a and 92b, respectively wrapped around portions of the slide rods 88a and 88b, are arranged to apply a biasing force that urges the transducer array assembly downward relative to the shoe assembly. Thus when levers 90a, 90b pivot inward during motion of the probe along a fillet surface of increasing radius with sufficient force to overcome the biasing force, the levers will cause the ultrasonic transducer array 60 to move upward, as seen in FIG. 8B. Conversely, as the fillet radius decreases, the levers 90a, 90b will pivot outward, allowing the springs 92a, 92b to urge the ultrasonic transducer array 60 downward, as seen in FIG. 7B.

Although the broad scope of the teaching herein encompasses the use of a single lever in some embodiments, the use of two levers reduces "racking" force on the slide stages to which the curved ultrasonic array is affixed.

The earlier analysis which derived a factor of 3.414 for situations in which the flange angle is 90° can be expanded to include composite parts that have flange angles other than 90 degrees, as shown in FIG. 5A. Note that Eq. (1) was arrived at by simply using the known ratio of the sides of a 45° right triangle (1:1:√2). This can be expressed more generally in terms of the angle between the hypotenuse and the flange surface (call φ) as:

$$C = \frac{1}{\sin\phi} R \qquad (6)$$

where the angle θ between the two flange surfaces, commonly called the "flange angle", is given by θ=2φ. Note that these are the same when the flange angle is 90°:

$$\sqrt{2} = 1/\sin 45$$

This can simply be substituted in the rest of the analysis, because for any given location the angle is a constant, so that the overall rate ratio between the motion of the fillet surface at H with a change in fillet radius R is $$\frac{dC}{dH} = \frac{dC}{dR}\frac{dR}{dH} = \frac{(\sin\phi)^{-1}}{(\sin\phi)^{-1} - 1} \qquad (8)$$

As the flange angle θ approaches 0°, the rate ratio approaches 1.0, whereas as the flange angle θ approaches 180°, the rate ratio approaches infinity (which can be seen as H=0 at this point). Thus, using a mechanical lever mechanism is not practical for the entire geometric range. In practice, however, flange angles rarely exceed 110° or go below 70°, which are lever ratios of 5.54 and 2.34 respectively. These are within the realm of a mechanism.

To adapt to the flange angle, the probe must be reactive to it. A probe with is continuously adaptive to both flange angle and fillet radius could be designed to comprise a parallelogram carriage (hinged) that follows the flange angle, and a mechanism to transfer this angle to the fulcrum point of the lever that moves the ultrasonic transducer array up and down along a translate aligned with the bisection of the angle of the hinged carriage.

Figure 9A:
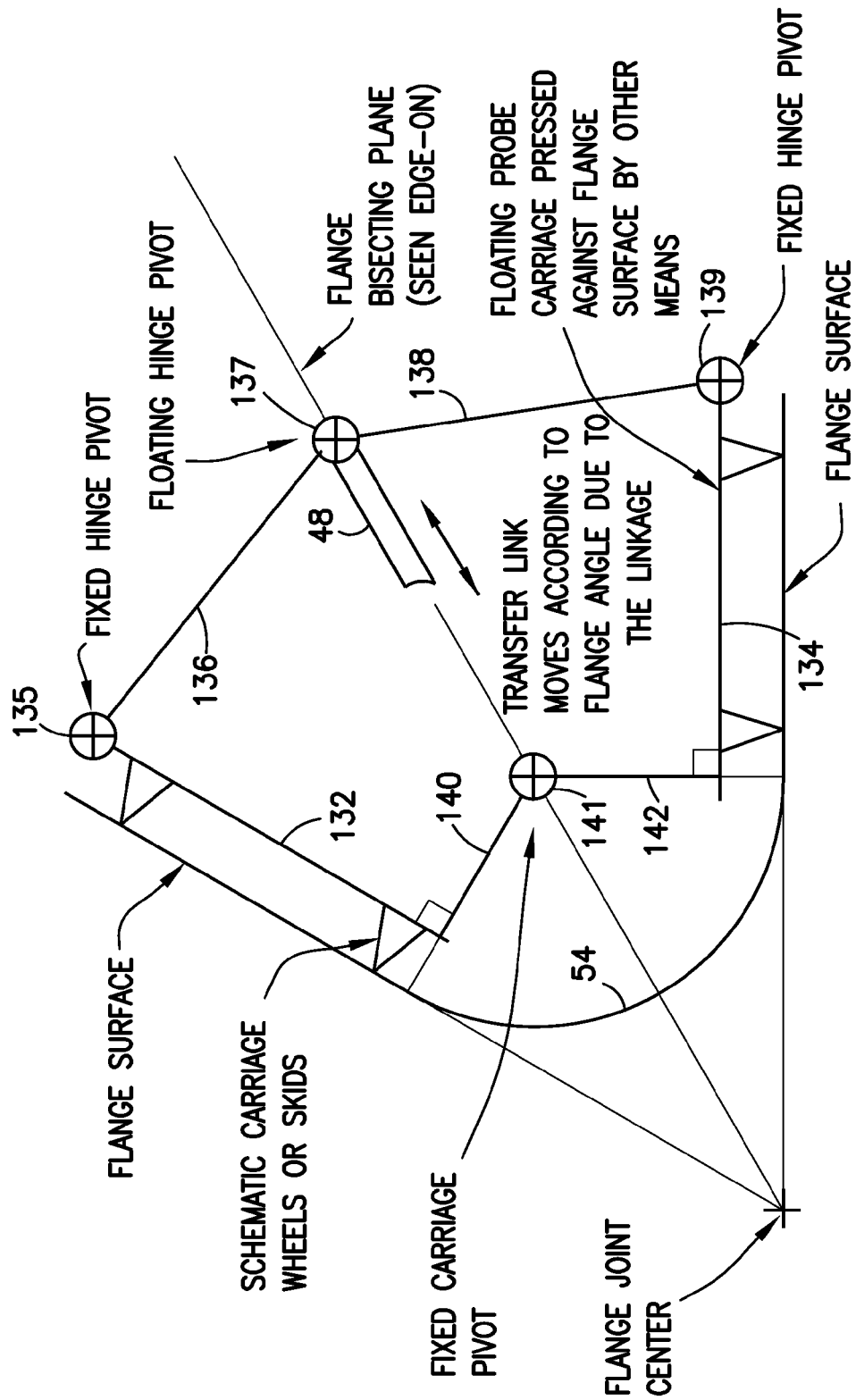
FIG. 9A is a diagram showing a side view of floating carriages and a flange angle sensing mechanism which can be utilized in conjunction with a continuously adaptive ultrasonic inspection device in situations where the flange angle of the inspected part is other than 90°.

FIG. 9A illustrates a method of adapting a probe to the flange angle of the part being inspected in accordance with one embodiment. The method involves two floating probe carriage sections 132 and 134 which are held against the two flange surfaces of a composite part in such a way that a flange angle transfer link 48 moves in dependence on the flange angle. In FIG. 9A, the two carriages 132, 134 are held together by means of a pair of rigid links 140 and 142, one end of each link being rigidly connected to the respective carriages and the other ends of which are pivotably coupled to a fixed carriage pivot 141. This allows the carriages 132 and 134 to fold to match the flange angle of the part being inspected.

The apparatus represented in FIG. 9A further comprises a hinge mechanism comprising: a rigid link 136 having one end pivotably coupled to carriage 132 by means of a fixed hinge pivot 135 and a rigid link 138 having one end pivotably coupled to carriage 134 by means of a fixed hinge pivot 139. The other ends of links 136 and 138 are pivotably coupled to a floating hinge pivot 137. The flange angle transfer link 48 can translate in tandem with the floating hinge pivot 137 in the directions indicated by the double-headed arrow in FIG. 9A. The hinge mechanism moves the flange angle transfer link toward and away from the flange joint in response to a change in flange angle. As explained below with reference to FIGS. 9B and 9C, the displacement of flange angle transfer link 48, which is a function of the flange angle, will cause an adjustable lever mechanism to change its state to produce a desired rate ratio during scanning of a joint fillet.

Figure 9B:
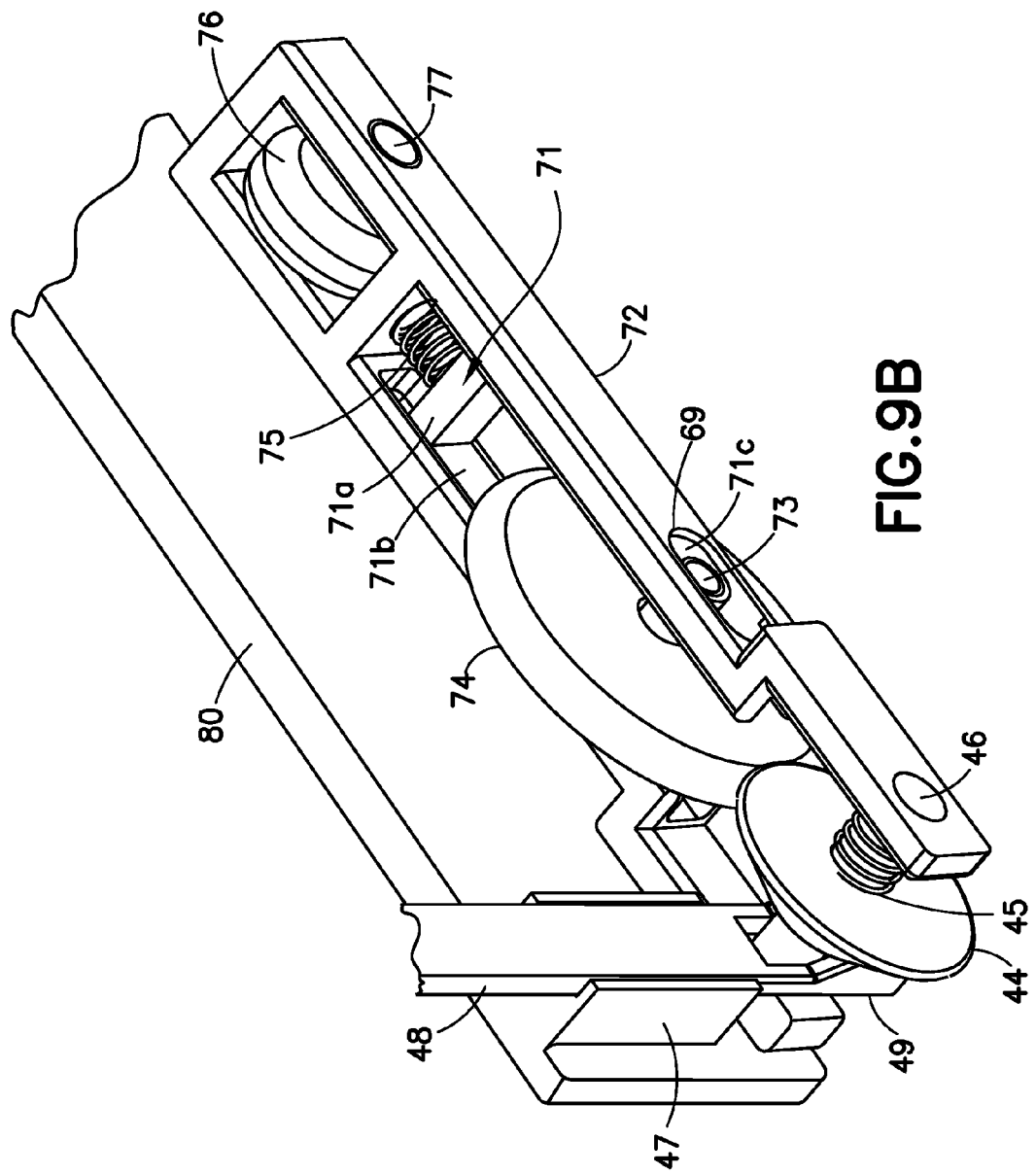
FIG. 9B is a diagram showing an isometric view of one embodiment of a flange angle sensing mechanism which can be utilized with the arrangement depicted in FIG. 9A.

FIG. 9B shows an isometric view of a flange angle sensing mechanism which can be utilized with the arrangement depicted in FIG. 9A to adjust transducer array position as a function of flange angle. While FIG. 9A showed one end of the flange angle transfer link 48 coupled to the floating hinge pivot 137, FIG. 9B shows the opposing end of flange angle transfer link 48. The flange angle transfer link 48 comprises a straight portion, the motion of which is constrained by a linear guide 47 (attached to probe body 80), and a split yoke 49. The yoke 49 has a pair of inclined surfaces (only one of which is partly visible in FIG. 9B) which bear against the end of a fulcrum cone 44. The fulcrum cone 44 is translatable on an axle 46, which is attached to lever 72 (described in the next paragraph). As the flange angle transfer link 48 moves up, the inclined surfaces of split yoke 49 bear against an end of the fulcrum cone 44, camming the fulcrum cone to translate in one direction along the axle 46. A spring 45 exerts a biasing force that urges the fulcrum cone 44 to translate along axle 46 in the opposite direction. As the flange angle transfer link 48 moves down, spring 45 pushes the fulcrum cone 44 in that opposite direction.

The motion of the fulcrum cone 44 along axle 46 in turn causes a surface wheel 74 to move toward or away from axle 46. The fulcrum cone 44 further comprises a conical surface which is contacted by the outer periphery of surface wheel 74. As previously described, the surface wheel 74 is designed to also bear against and roll along a fillet surface during ultrasonic inspection of a composite part joint fillet. In the embodiment shown in FIG. 9B, the surface wheel 74 is attached to an axle 73. Opposing ends of axle 73 reside inside respective bushings 71c (only one of which is visible in FIG. 9B), which bushings are attached to or incorporated in ends of respective arms 71b (only one of which is visible in FIG. 9B) of a U-shaped carriage 71. The carriage 71, in turn, is translatably coupled to the lever 72. Bushings 71c of carriage 71 are seated in and translatable back and forth with respect to respective slots 69 (only one of which is visible in FIG. 9B). Carriage 71 further comprises a base member 71a that connects the proximal ends of arms 71b to each other. Accordingly, it should be understood that the surface wheel 74 is carried by and rotatable relative to the carriage 71.

The ends of the arms of lever 72 support opposing ends of the axle 46 on which the fulcrum cone 44 translates, while the distal end of lever 72 supports opposing ends of an axle 77 on which the array positioning wheel 76 is mounted. A spring 75, placed between base member 71a of carriage 71 and an opposing crosspiece of lever 72, urges the carriage 71 to translate in a direction such that the surface wheel 74 is held against the fulcrum cone 44.

As previously described, the motion of the fulcrum cone 44 along axle 46 causes the surface wheel 74 to move toward or away from axle 46 during up or down movement of the flange angle transfer link 48 as the carriages (items 132, 134 in FIG. 9a) are adjusted to match the flange angle (other than 90°) of the composite part being inspected. This motion of surface wheel 74 in turn changes the distance D separating the axis of rotation of surface wheel 74 (i.e., the axis of axle 73) from the axis of rotation of the lever 72 (i.e., the axis of axle 46). The distance D is controlled by the position of the fulcrum cone 44 against which the surface wheel 74 rolls. The position of the fulcrum cone 44 is controlled by the position of the flange angle transfer link 48, which in turn is controlled by the flange angle of the part being inspected. The surface wheel 74 rides both on the fulcrum cone 44 and the part fillet (not shown in FIG. 9C). Because the cone axle is located on the fixed pivot point of the lever (the fulcrum), the surface wheel 74 moves the correct distance along the lever 72 no matter what the angle of the lever.

Figure 9C:
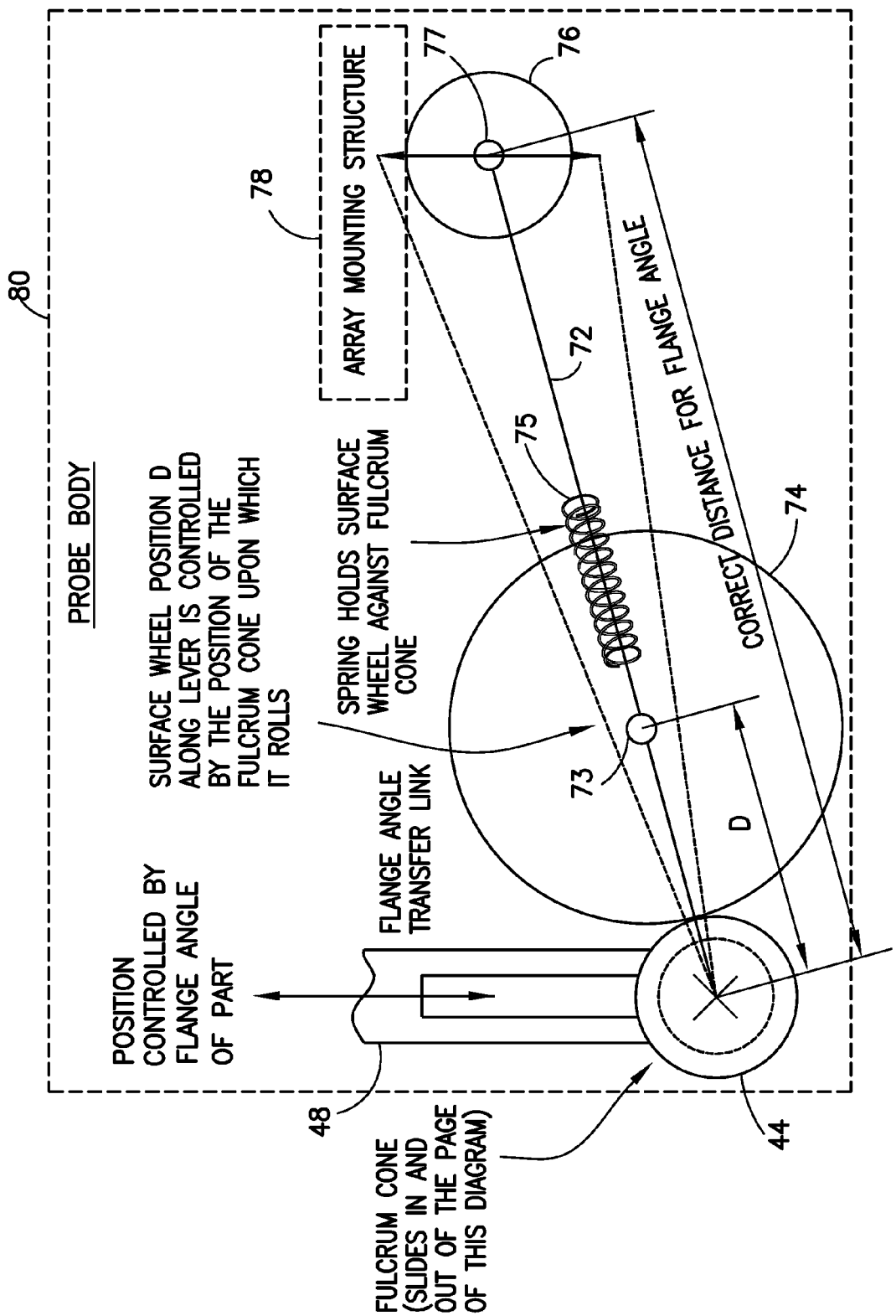
FIG. 9C is a diagram showing a principle of operation of a lever design involving a surface wheel adjustably mounted to the lever, its position along the lever being a function of the flange angle of the part being inspected.

The array positioning wheel 76 is rotatably coupled to the distal portion of lever 72. As shown in FIG. 9C, the array positioning wheel 76 bears against and rolls along a surface of a transducer array support structure 78. The transducer array support structure 78 is translatably coupled to the probe shoe or body 80. When the surface wheel 74 moves up or down by a distance X, the array positioning wheel 76 and the array support structure 78 in contact therewith move up or down by a distance equal to the product of a rate ratio and distance X. That rate ratio is a function of distance D. Since distance D is a function of the flange angle, the rate ratio will be also. Once the flange angle transfer link has been translated by the distance required to establish the desired rate ratio, the curved transducer array will move toward or away from the joint intersection by the appropriate distance as the fillet surface "moves" (i.e., changes radius) along the angle halfway between one flange surface and the other. This keeps the geometric alignment of the curved ultrasonic transducer array with the part fillet correct, i.e., the ultrasonic transducer array is moved such that it keeps its focus on the center of the part fillet radius.

The angle-dependent rate ratio of Eq. (8) can be exactly duplicated by adjusting the shape of the fulcrum "cone", the angle and shape of the split yoke on the transfer link, and the dimensions of the hinge mechanism which moves the flange angle transfer link.

The ultrasonic probe described above can position a curved ultrasonic transducer array adaptively according to both the local fillet radius and flange angle. This device is adaptively sensitive to a varying radius as it is moved along a part. In accordance with one embodiment, the device is self-adjusting as it is moved along a part that has continuously changing fillet radii at the right-angle joint of two planar portions of a part. In accordance with another embodiment, the device can also adapt to varying joint angles. This feature can be employed to speed up the inspection process to a significant degree (an order of magnitude or more) and enable the use of automation. In many applications, multiple probes can be replaced by a single adaptive probe, saving inspection time, cost of installation, and cost of maintenance. The angle-adaptive version has the potential to replace a large number of existing probes with one device. Additionally, since this is a simple mechanical solution, it precludes the need for complex and failure-prone electromechanical methods to accomplish the required motion of the curved ultrasonic transducer array. The disclosed devices have the ability to keep a curved ultrasonic transducer array in the correct geometric relationship with a part radius of varying size, as the device is scanned lengthwise along the joint at arbitrary speed, thus increasing production part inspection rate by over an order of magnitude. The angle-adaptive version embodies a probe design that can be used to inspect hard-tooled inside fillets on the majority of all airplane parts, potentially replacing the hundreds of manual systems currently in use with a single, common design.

In accordance with one application, the apparatus described above can be used in the non-destructive inspection of an integrally stiffened wing box of an aircraft e.g., a horizontal stabilizer made of composite material. A portion of a generalized integrally stiffened wing box 2 is depicted in FIG. 10. The depicted integrally stiffened wing box comprises a top skin 4 and a bottom skin 6 connected by a plurality of internal vertical support elements, hereinafter referred to as "spars". Each spar comprises a web 8 and respective pairs of filleted join regions 10 (also called "spar radii" herein), which connect the spar web 8 to the top and bottom skins. As used herein, the terms "top skin" and "bottom skin" refer to the relative positions of two skins of a wing box during inspection, not when the wing box is installed on an airplane (i.e., a wing box may be inverted for inspection).

In accordance with one embodiment, an ultrasonic probe (comprising, e.g., a shoe assembly and an ultrasonic transducer array assembly as shown in FIG. 7A) is transported down the length of a tunnel through the interior of a hollow composite structure. For this type of inspection, the probe is carried by a trailer vehicle (not shown in FIG. 10) placed inside the hollow structure 2. This trailer vehicle can be characterized as being "active" in the sense that equipment it carries is actively performing a scanning function. The array needs to be acoustically coupled to the surface being inspected. This is accomplished by providing a column of water that flows between the array and the inspected part. An automated tractor vehicle (also not shown in FIG. 10) moves the active trailer vehicle along the spar web 8.

In FIG. 10, portions of the interior surfaces of the part which need to be inspected can be seen. Each spar may need to have all four filleted join regions 10 and each web 8 inspected. This is a challenging inspection as each cavity is essentially a long rectangular tunnel that may increase or decrease in cross section as one moves from one end to the other. The top and bottom skins 4 and 6 can be inspected from the exterior using conventional NDI techniques which are not part of this disclosure In accordance with one embodiment for inspecting structures of the type shown in FIG. 10, an external motorized and computer-controlled tractor is magnetically coupled to an internal active trailer that holds and positions the ultrasonic probe on the interior of the part. Also, there is an internal passive trailer on the opposite side of the spar that is magnetically coupled through the spar to the active trailer and also magnetically coupled through the skin to the tractor. This three-part system gives a very stable system for positioning and moving the ultrasonic transducer array. One embodiment of such a three-part system will now be described with reference to FIGS. 11 and 12.

Figure 12:
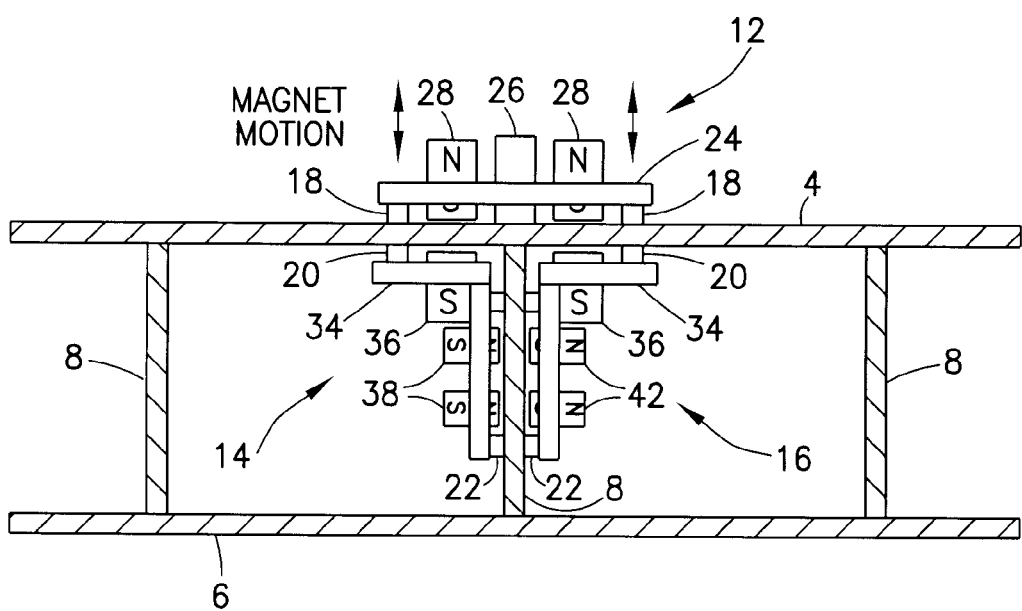
FIG. 12 is a diagram showing an end view of the tractor-trailer configuration depicted on the left-hand side of FIG. 11 (with respective inverted trailer vehicles disposed on both sides of a spar).

FIG. 11 shows side views of a tractor-trailer configuration in accordance with one embodiment in two different inspection situations (motor actuators are not shown). The automated NDI inspection system comprises a traction-motor powered tractor vehicle 12, which rides on the external surface of top skin 4 or bottom skin 6 of integrally stiffened wing box 2, and a pair of trailer vehicles (only trailer vehicle 14 is visible in FIG. 11, the other being hidden behind a spar web 8), which ride along an internal surface of the top or bottom skin. The left-hand side of FIG. 11 shows an inspection scenario wherein the tractor vehicle 12 is outside the integrally stiffened wing box in a non-inverted position while the trailer vehicles are inside the integrally stiffened wing box in inverted positions; the right-hand side of FIG. 11 shows an inspection scenario wherein the tractor vehicle 12 is outside the integrally stiffened wing box in an inverted position while the trailer vehicles are inside the integrally stiffened wing box in non-inverted positions. FIG. 12 shows an end view of the tractor-trailer configuration depicted on the left-hand side of FIG. 11, with inverted trailer vehicles 14 and 16 disposed on opposite sides of the spar web.

In the inspection scenario depicted in FIG. 12 (and the left-hand side of FIG. 11), idler wheels 18 of tractor vehicle 12 contact and roll on the external surface of top skin 4 while vertical idler wheels 20 of inverted trailer vehicles 14 and 16 (only one such idler wheel is visible in FIG. 12 for each trailer vehicle) contact and roll on the internal surface of top skin 4, and the horizontal idler wheels 22 roll on the spar web surface. The right-hand side of FIG. 11 shows an alternative situation wherein idler wheels 18 of the inverted tractor vehicle 12 contact and roll on the external surface of bottom skin 6 while vertical idler wheels 20 of trailer vehicle 14 (and also idler wheels of trailer vehicle 16 not visible in FIG. 11) contact and roll on the internal surface of bottom skin 6, and the horizontal idler wheels 22 roll on the spar web surface.

In accordance with the embodiment partly depicted in FIGS. 11 and 12, the tractor vehicle 12 comprises a frame 24. Four idler wheels 18 (only two of which are visible in each of FIGS. 11 and 12) are rotatably coupled to frame 24 in a conventional manner. (Alternative embodiments may include more idler wheels.) The idler wheels 18 are made of plastic and have smooth contact surfaces. Tractor vehicle motion is enabled by driving a drive wheel 26 (also rotatably coupled to frame 24) to rotate. Drive wheel 26 is coupled to a motor 30 via a transmission (not shown). The drive wheel 26 is positioned on the frame 24 so that it is in frictional contact with skin 4 or 6 when idler wheels 18 are in contact with the same skin. The drive wheel is made of synthetic rubber material. The surface of the drive wheel may have a tread pattern. In addition, the tractor vehicle 12 carries multiple permanent magnets 28. Each permanent magnet 28 has North and South poles, respectively indicated by letters "N" and "S" in the drawings.

Still referring to FIGS. 11 and 12, each trailer vehicle 14, 16 is comprised of a frame 34. For each trailer vehicle, two vertical idler wheels 20 (only one of which is visible in FIG. 12) and four horizontal idler wheels 22 (only two of which are visible in FIG. 12) are rotatably coupled to frame 34 in a conventional manner. (Alternative embodiments may include more idler wheels.) Each trailer vehicle 14, 16 carries multiple vertically mounted permanent magnets 36, the North poles of which are magnetically coupled to the South poles of confronting permanent magnets 28 carried by the tractor vehicle 12. In the design described by FIGS. 11 and 12, each trailer has two vertically mounted permanent magnets 36, but other designs may use different configurations. The positions and pole orientations of the magnets may have other configurations as long as the N-S pairing and relative alignment of the magnets between the tractor and trailer are preserved.

As seen in FIG. 12, in addition to being magnetically coupled to the tractor vehicle 12, the trailer vehicles 14 and 16 are magnetically coupled to each other using additional sets of permanent magnets 38 and 42. As seen in FIG. 11, trailer vehicle 14 carries four horizontally mounted permanent magnets 38. Trailer vehicle 16 also carries four horizontally mounted permanent magnets 42 (only two of which are visible in FIG. 12), the poles of which are respectively magnetically coupled to opposing poles of the permanent magnets 38 on trailer vehicle 14. This magnetic coupling produces an attraction force that holds idler wheels 22 of trailer vehicles 14 and 16 in contact with opposing surfaces of an intervening spar.

As seen in FIG. 11, trailer vehicle 14 further carries an ultrasonic probe 40 of the type shown in FIG. 7A. As previously noted, the ultrasonic transducer array of probe 40 will be acoustically coupled to the surface being inspected. For example, the inspected region is covered with a constant stream of water to acoustically couple the ultrasonic probe to a filleted join region 10. Magnetically coupled systems are well suited for operation with water in the environment.

As the tractor vehicle is driven to travel along a desired path on the outer surface of the top or bottom skin, it pulls the inner trailer vehicles along. The magnetic coupling system described above keeps the inverted vehicle(s) in contact with the surface it rides on. For wing box applications, two magnetically coupled trailer vehicles can be used, one on each side of the spar, as shown in FIG. 12. This allows the system to take advantage of the internal structure of the scanned object as a guide to allow the system to track properly along the surface.

The system partly depicted in FIGS. 11 and 12 further comprises means (not shown) for automatically adapting to the variable thickness of the intervening skin or panel (i.e., top skin 4 or bottom skin 6) by raising or lowering the magnets (which magnet motion is indicated by double-headed arrows in FIG. 11) on the tractor vehicle as it moves along the structure being inspected. Further details concerning the trailer-tractor configuration depicted in FIGS. 11 and 12 (and alternative embodiments) are disclosed in U.S. patent application Ser. No. 13/313,267, the disclosure of which is incorporated by reference herein in its entirety.

The X-axis motion (the X axis being parallel to the spar radius being inspected if the spar radius is linear) is provided by the tractor vehicle of the system, which uses data from a rotational encoder attached to an idler wheel on the trailer vehicle. The trailer component is pulled by the tractor and carries the probe assembly. The X-motion drive motor can be a programmable stepper motor that can communicate with a computer through a serial communications interface. An operator or automated path planning system specifies the desired incremental movements, direction, and an optional final goal position of the tractor-trailer system through a motion control software application. The X-axis positioning is controlled using proportional feedback of the encoder count data.

Figure 13:
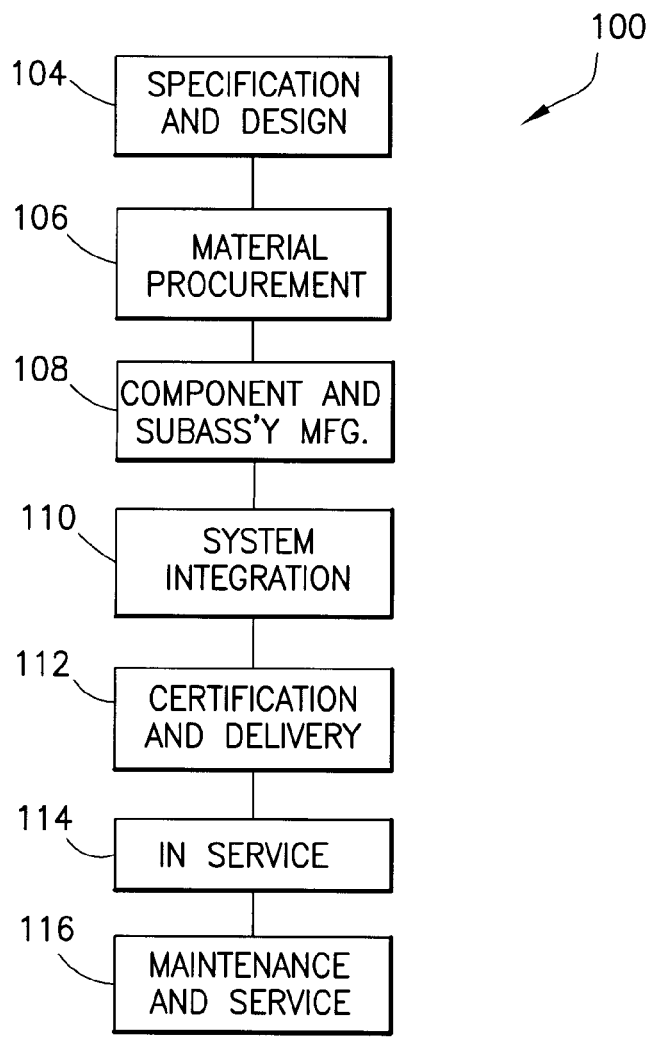
FIG. 13 is a flow diagram of an aircraft production and service methodology.
Figure 14:
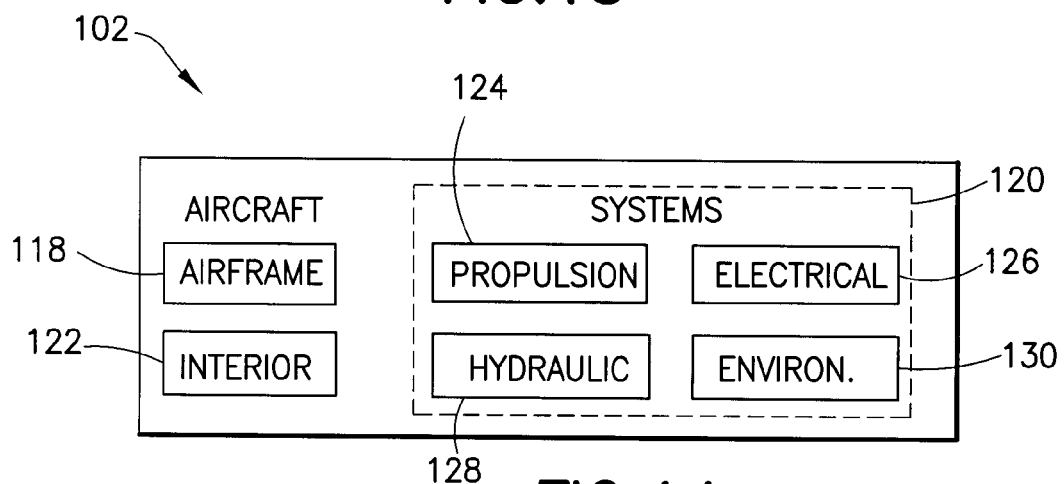
FIG. 14 is a block diagram showing systems of an aircraft.

The system and method disclosed above may be employed in an aircraft manufacturing and service method 100 as shown in FIG. 13 for inspecting parts of an aircraft 102 as shown in FIG. 14. During pre-production, exemplary method 100 may include specification and design 104 of the aircraft 102 and material procurement 106. During production, component and subassembly manufacturing 108 and system integration 110 of the aircraft 102 takes place. Thereafter, the aircraft 102 may go through certification and delivery 112 in order to be placed in service 114. While in service by a customer, the aircraft 102 is scheduled for routine maintenance and service 116 (which may also include modification, reconfiguration, refurbishment, and so on).

Each of the processes of method 100 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 14, the aircraft 102 produced by exemplary method 100 may include an airframe 118 with a plurality of systems 120 and an interior 122. Examples of high-level systems 120 include one or more of the following: a propulsion system 124, an electrical system 126, a hydraulic system 126, and an environmental control system 130. Any number of other systems may be included. Although an aerospace example is shown, the principles of the invention may be applied to other industries, such as the automotive industry.

Apparatus and methods embodied herein may be employed during any one or more of the stages of the production and service method 100. For example, components or subassemblies corresponding to production process 108 may be fabricated or manufactured in a manner similar to components or subassemblies produced while the aircraft 102 is in service. Also, one or more apparatus embodiments, method embodiments, or a combination thereof may be utilized during the production stages 108 and 110, for example, by substantially expediting assembly of or reducing the cost of an aircraft 102. Similarly, one or more of apparatus embodiments, method embodiments, or a combination thereof may be utilized while the aircraft 102 is in service, for example and without limitation, during maintenance and service 116.

While ultrasonic inspection devices have been described with reference to various embodiments, it will be understood by those skilled in the art that various changes may be made and equivalents may be substituted for elements thereof without departing from the scope of the teachings herein. In addition, many modifications may be made to adapt the teachings herein to a particular situation without departing from the scope thereof. Therefore it is intended that the claims not be limited to the particular embodiments disclosed herein.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices comprising a processing unit (e.g., a central processing unit) and some form of memory (i.e., computer-readable medium) for storing a program which is readable by the processing unit.

As used in the claims, the term "chassis" means a platform or frame that is movable, e.g., by rolling or sliding. For example, trailer vehicle 14 (see FIG. 11) is one example of a chassis.

The method claims set forth hereinafter should not be construed to require that the steps recited therein be performed in alphabetical order (alphabetical ordering in the claims is used solely for the purpose of referencing previously recited steps) or in the order in which they are recited. Nor should they be construed to exclude any portions of two or more steps being performed concurrently or alternatingly.

The invention claimed is:

1. An inspection apparatus comprising:
   a chassis;
   a shoe assembly comprising a frame attached to said chassis, first and second slide rods attached to said frame, and a first axle attached to said frame;
   an array support structure comprising first and second slide stages which are translatably coupled to said first and second slide rods respectively;
   a transducer array assembly which is attached to said array support structure;
   first biasing means for urging said array support structure to translate relative to said shoe assembly in a first direction; and
   a first lever assembly which is pivotably coupled to said first axle of said shoe assembly and which contacts said first slide stage over a range of angular positions of said first lever assembly.

2. The apparatus as recited in claim 1, wherein said shoe assembly comprises a second axle, said apparatus further comprising a second lever assembly which is pivotably coupled to said second axle of said shoe assembly and contacts said second slide stage over a range of angular positions of said second lever assembly, and wherein said array support structure translates relative to said shoe assembly in a second direction opposite to said first direction when a first net force exerted by said first and second lever assemblies is greater than and opposite to a second net force exerted by said first biasing means.

3. The apparatus as recited in claim 1, wherein said first lever assembly comprises a lever, said lever comprising a distal portion in contact with said first slide stage, a proximal portion pivotably coupled to said first axle, and an intermediate portion which connects said distal and proximal portions.

4. The apparatus as recited in claim 3, wherein said intermediate portion of said lever has a curved surface that projects outside said shoe assembly.

5. The apparatus as recited in claim 3, further comprises a wheel which is rotatably coupled to said intermediate portion of said lever, wherein a portion of said wheel projects outside said shoe assembly.

6. The apparatus as recited in claim 3, further comprising a carriage translatably coupled to said lever, second biasing means for urging said carriage to translate toward said proximal portion of said lever, and a wheel rotatably coupled to said carriage, wherein a portion of said wheel projects outside said shoe assembly.

7. The apparatus as recited in claim 6, wherein said chassis comprises:
   first and second carriages;
   a first fixed pivot which pivotably couples said first carriage to said second carriage;
   first and second links each having first and second ends;
   a second fixed pivot which pivotably couples said first carriage to said first end of said first link;
   a third fixed pivot which pivotably couples said second carriage to said first end of said second link;
   a floating pivot which pivotably couples said second end of said first link to said second end of said second link;
   a flange angle transfer link which translates in tandem with said floating pivot;
   a fulcrum cone which is translatably coupled to said first axle of said shoe assembly and which is in contact with said flange angle transfer link and said wheel; and
   third biasing means for urging said fulcrum cone into contact with said flange angle transfer link.

8. The apparatus as recited in claim 1, wherein said first lever assembly comprises:
   a lever comprising a distal portion, a proximal portion pivotably coupled to said first axle, and an intermediate portion which connects said distal and proximal portions; and
   a first wheel rotatably coupled to said distal portion of said lever and in contact with said transducer array assembly.

9. The apparatus as recited in claim 8, wherein said intermediate portion of said lever has a curved surface that projects outside said shoe assembly.

10. The apparatus as recited in claim 8, wherein said first lever assembly further comprises a second wheel which is rotatably coupled to said intermediate portion of said lever, a portion of said second wheel projecting outside said shoe assembly.

11. The apparatus as recited in claim 8, wherein said first lever assembly further comprises:
   a carriage translatably coupled to said lever;
   second biasing means for urging said carriage to translate toward said proximal portion of said lever; and
   a second wheel rotatably coupled to said carriage, a portion of said second wheel projecting outside said shoe assembly.

12. The apparatus as recited in claim 11, wherein said chassis comprises:
   first and second carriages;
   a first fixed pivot which pivotably couples said first carriage to said second carriage;
   first and second links each having first and second ends;
   a second fixed pivot which pivotably couples said first carriage to said first end of said first link;
   a third fixed pivot which pivotably couples said second carriage to said first end of said second link;
   a floating pivot which pivotably couples said second end of said first link to said second end of said second link;
   a flange angle transfer link which translates in tandem with said floating pivot;

a fulcrum cone which is translatably coupled to said first axle of said shoe assembly and which is in contact with said flange angle transfer link and said second wheel; and third biasing means for urging said fulcrum cone into contact with said flange angle transfer link.

13. An inspection system comprising:

a chassis comprising a plurality of rolling elements having respective axes of rotation which are perpendicular to a rolling direction of said chassis;

a frame which is supported by said chassis;

a transducer array which is translatably coupled to and carried by said frame;

biasing means for producing a biasing force that urges said transducer array to translate relative to said frame wee in a first direction; and first and second levers having respective curved camming surfaces arranged to exert a net force that opposes said biasing force, wherein said first and second levers are pivotably coupled to said frame, wherein said transducer array will translate in a second direction opposite to said first direction when said net force exerted by said curved camming surfaces of said first and second levers is greater than said biasing force.

14. The system as recited in claim 13, further comprising a fulcrum cone for adjusting a position of said curved camming surface of said first lever relative to said frame in dependence on a flange angle of a composite part being inspected.

15. The system as recited in claim 13, wherein said transducer array comprises a multiplicity of ultrasonic transducers distributed along a curve.

16. The system as recited in claim 13, further comprising a joint fillet of a structure made of composite material, said joint fillet comprising a radiused surface whose radius varies along the length of said joint fillet, wherein said curved camming surfaces of said first and second levers are in contact with respective portions of said surface of said joint fillet.

17. An inspection apparatus comprising:

a chassis comprising a plurality of rolling elements having respective axes of rotation which are perpendicular to a rolling direction of said chassis;

a frame which is supported by said chassis;

a transducer array assembly which is translatably coupled to said frame;

one or more springs that urge said transducer array assembly to translate relative to said frame in a first direction normal to said rolling direction; and one or more levers which are rotatable relative to said frame through a range of angular positions for causing said transducer array assembly to translate in a second direction opposite to said first direction, each of said one or more levers comprising a proximal portion pivotably coupled to said shoe assembly and a distal portion in contact with said transducer array assembly, wherein said transducer array assembly will translate in said second direction when a first net force exerted by said one or more levers is greater than and opposite to a second net force exerted by said one or more springs.

18. The apparatus as recited in claim 17, further comprising first and second slide rods attached to said frame, wherein said transducer array assembly comprises an array support structure, a transducer array attached to said array support structure, and first and second linear bearings respectively translatable along said first and second slide rods.

19. A method for inspecting a joint fillet having a surface the radius of which varies along a length of the joint fillet, performed using an inspection unit comprising a frame and a curved transducer array that is movable relative to the frame and has a center, said method comprising:

(a) activating a motor to cause the inspection unit to move along the length of the joint fillet from a first longitudinal position, whereat the curved transducer array is directed toward a first target portion of the joint fillet having a surface with a first radius, to a second longitudinal position, whereat the curved transducer array is directed toward a second target portion of the joint fillet having a surface with a second radius different than said first radius;

(b) during step (a), continuously moving the curved transducer array relative to the frame so that the center of the curved transducer array and the center of the variable radius of the joint fillet are the same point in space; and (c) activating the curved transducer array when the inspection unit is in said first and second longitudinal positions to interrogate said first and second target positions respectively.

20. The method as recited in claim 19, wherein the curved transducer array moves relative to the frame in response to a varying force produced by contact with portions of the surface of the joint fillet which vary in radius.

21. The method as recited in claim 19, wherein the distance that the curved transducer array is moved relative to the frame during step (a) is equal to a product of a factor times a difference between a first distance of a center of said first radius of the joint fillet from a reference line and a second distance of a center of said second radius of the joint fillet from said reference line.

\* \* \* \* \*